(12) United States Patent
Petersen et al.

(10) Patent No.: US 11,207,269 B2
(45) Date of Patent: Dec. 28, 2021

(54) MEDICAL USE OF SPLA2 HYDROLYSABLE LIPOSOMES

(71) Applicant: BIO-BEDST APS, Vejle (DK)

(72) Inventors: Morten Just Petersen, Værløse (DK); Fredrik Melander, Bunkeflostrand (SE); Anders Falk Vikbjerg, Greve (DK); Sune Allan Petersen, Greve (DK); Mogens Winkel Madsen, Virum (DK)

(73) Assignee: BIO-BEDST APS, Hørsholm (DK)

( * ) Notice: Subject to any disclaimer, the term of this patent is extended or adjusted under 35 U.S.C. 154(b) by 0 days.

(21) Appl. No.: 16/360,836

(22) Filed: Mar. 21, 2019

(65) Prior Publication Data

US 2019/0343766 A1  Nov. 14, 2019

Related U.S. Application Data

(62) Division of application No. 13/497,031, filed as application No. PCT/DK2010/050237 on Sep. 16, 2010.

(30) Foreign Application Priority Data

Sep. 17, 2009 (DK) ............................ PA 2009 01037

(51) Int. Cl.
*A61K 9/127* (2006.01)
*A61K 31/282* (2006.01)
(Continued)

(52) U.S. Cl.
CPC .......... *A61K 9/1271* (2013.01); *A61K 9/0019* (2013.01); *A61K 9/1272* (2013.01);
(Continued)

(58) Field of Classification Search
CPC .... A61K 9/127; A61K 9/1271; A61K 31/282; A61K 9/1272; A61K 9/0019; A61K 45/06; A61K 33/24; A61P 35/00
See application file for complete search history.

(56) References Cited

U.S. PATENT DOCUMENTS 4,880,635 A    11/1989  Janoff et al.
4,963,362 A *  10/1990  Rahman ................. A61K 9/127
                                                    264/4.1
(Continued)

FOREIGN PATENT DOCUMENTS

CN    102002490 A    4/2011
EP     1550731 A1    7/2005
(Continued)

OTHER PUBLICATIONS

Terwogt, JMM et al Cancer Chemother. Pharmacol. 49, pp. 201-210, 2002.*
(Continued)

*Primary Examiner* — Gollamudi S Kishore
(74) *Attorney, Agent, or Firm* — Clark & Elbing LLP

(57) ABSTRACT

The present invention relates to medical use of liposomes, more particular the first medical use of sPLA2 hydrolysable liposomes. Such liposomes may be used for targeted delivery of therapeutic agents to cancerous tissue and in such embodiments; the therapeutic agents are typically small molecule antitumor agents. Other aspects of the inventions relates to methods of reducing the side effects of therapeutic agents, e.g. reducing nephrotoxicity, neurotoxicity and gastrointestinal toxicity of a therapeutic agent. Yet another aspect of the present invention relate to methods of prolonging the therapeutic effect of a therapeutic agent.

18 Claims, 20 Drawing Sheets

(51) Int. Cl.
  *A61K 9/00* (2006.01)
  *A61K 45/06* (2006.01)
  *A61K 33/243* (2019.01)

(52) U.S. Cl.
  CPC .......... *A61K 31/282* (2013.01); *A61K 33/243* (2019.01); *A61K 45/06* (2013.01)

(56) References Cited

U.S. PATENT DOCUMENTS

| | | | |
|---|---|---|---|
| 5,858,397 A * | 1/1999 | Lim ................ | A61K 9/127 424/450 |
| 6,027,726 A * | 2/2000 | Ansell .............. | A61K 9/1271 424/179.1 |
| 6,911,306 B1 | 6/2005 | Vertino | |
| 7,239,986 B2 | 7/2007 | Golub et al. | |
| 7,273,620 B1 | 9/2007 | Zhigaltsev et al. | |
| 7,709,616 B2 | 5/2010 | Bentwich et al. | |
| 8,445,198 B2 | 5/2013 | Knudsen | |
| 9,598,734 B2 | 3/2017 | Knudsen | |
| 9,725,769 B1 | 8/2017 | Knudsen | |
| 9,820,941 B2 | 11/2017 | Madsen et al. | |
| 2001/0051344 A1 | 12/2001 | Shalon et al. | |
| 2002/0164663 A1 | 11/2002 | Fuqua et al. | |
| 2003/0026831 A1* | 2/2003 | Lakkaraju ........... | A61K 9/127 424/450 |
| 2003/0073083 A1 | 4/2003 | Tamayo et al. | |
| 2003/0147945 A1* | 8/2003 | Tardi ................ | A61K 9/127 424/450 |
| 2004/0018525 A1 | 1/2004 | Wirtz et al. | |
| 2004/0022842 A1 | 2/2004 | Eriguchi et al. | |
| 2004/0072722 A1 | 4/2004 | Kornblith et al. | |
| 2005/0118250 A1* | 6/2005 | Tardi ................ | A61K 9/127 424/450 |
| 2005/0176669 A1 | 8/2005 | Al-Murrani | |
| 2005/0222396 A1* | 10/2005 | Bao ................. | A61K 51/0478 534/11 |
| 2005/0260586 A1 | 11/2005 | Demuth et al. | |
| 2005/0260646 A1 | 11/2005 | Baker et al. | |
| 2006/0105360 A1 | 5/2006 | Croce et al. | |
| 2006/0121511 A1 | 6/2006 | Lee et al. | |
| 2007/0148196 A1* | 6/2007 | Haas ................ | B01J 13/0086 424/401 |
| 2007/0172844 A1 | 7/2007 | Lancaster et al. | |
| 2007/0286898 A1* | 12/2007 | Takagi .............. | A61K 9/0019 424/450 |
| 2008/0085295 A1 | 4/2008 | Melvik et al. | |
| 2008/0227663 A1 | 9/2008 | Tisone et al. | |
| 2008/0306006 A1 | 12/2008 | Croce et al. | |
| 2009/0023149 A1 | 1/2009 | Knudsen | |
| 2009/0162425 A1* | 6/2009 | Divi ................. | A61K 49/0032 424/450 |
| 2009/0221435 A1 | 9/2009 | Baskerville et al. | |
| 2009/0239223 A1 | 9/2009 | Gehrmann et al. | |
| 2010/0189771 A1* | 7/2010 | Mayer .............. | A61K 31/4745 424/450 |
| 2010/0240043 A1 | 9/2010 | Rotter et al. | |
| 2011/0123990 A1 | 5/2011 | Baker et al. | |
| 2012/0009243 A1 | 1/2012 | Vikbjerg et al. | |
| 2012/0046186 A1 | 2/2012 | Pelham et al. | |
| 2012/0214703 A1 | 8/2012 | Croce et al. | |
| 2012/0302626 A1 | 11/2012 | Dave et al. | |
| 2013/0053275 A1 | 2/2013 | Knudsen | |
| 2013/0059015 A1 | 3/2013 | Lancaster et al. | |
| 2014/0134166 A1 | 5/2014 | Gutin et al. | |
| 2014/0294730 A1 | 10/2014 | Slack-Davis et al. | |
| 2015/0353928 A1 | 12/2015 | Weiner | |
| 2016/0199399 A1 | 7/2016 | Knudsen | |
| 2017/0283884 A1 | 10/2017 | Knudsen | |
| 2018/0087113 A1 | 3/2018 | Knudsen | |
| 2018/0202004 A1 | 7/2018 | Knudsen | |

FOREIGN PATENT DOCUMENTS

| | | |
|---|---|---|
| EP | 2 123 258 * | 8/2008 |
| EP | 2008/073177 A2 | 7/2009 |
| EP | 2081950 B1 | 3/2013 |
| JP | 2001-17171 A | 1/2001 |
| KR | 2007-0036055 A | 4/2007 |
| RU | 2528247 C2 | 9/2014 |
| WO | WO-99/30686 A1 | 6/1999 |
| WO | WO-00/35473 A2 | 6/2000 |
| WO | WO-03/082078 A2 | 10/2003 |
| WO | WO-2005/000266 A2 | 1/2005 |
| WO | WO-2005/014856 A1 | 2/2005 |
| WO | WO-2005/066371 A2 | 7/2005 |
| WO | WO-2005/087948 A2 | 9/2005 |
| WO | WO-2005/094863 A1 | 10/2005 |
| WO | WO-2007/072225 A2 | 6/2007 |
| WO | WO-2008/073177 A2 | 6/2008 |
| WO | WO-2008/073629 A2 | 6/2008 |
| WO | WO-2008/112283 A2 | 9/2008 |
| WO | WO-2008/138578 A2 | 11/2008 |
| WO | WO-2009/036332 A1 | 3/2009 |
| WO | WO-2009/080437 A1 | 7/2009 |
| WO | WO-2009/141450 A2 | 11/2009 |
| WO | WO-2011/032563 A1 | 3/2011 |
| WO | WO-2011/047689 A2 | 4/2011 |
| WO | WO-2011/098578 A2 | 8/2011 |
| WO | WO-2011/135459 A2 | 11/2011 |
| WO | WO-2012/024543 A1 | 2/2012 |
| WO | WO-2012/106718 A2 | 8/2012 |
| WO | WO-2012/109233 A2 | 8/2012 |
| WO | WO-2012/163541 A1 | 12/2012 |
| WO | WO-2013/130465 A2 | 9/2013 |
| WO | WO-2014/195032 A1 | 12/2014 |

OTHER PUBLICATIONS

Veal, GJ., et al British Journal of Cancer, 84 (8), pp. 1029-1035, 2001.*

Andresen, T.L., et al Progress in Lipid Research, 44, pp. 68-97, 2005.*

Trosco, J.E., et al in Mutation Research 480-481, pp. 219-229, 2001.*

Arienti et al., "Activity of lipoplatin in tumor and in normal cells in vitro," Anti-Cancer Drugs. 19(10):983-990 (2008) (8 pages).

Abba et al., "Gene expression signature of estrogen receptor alpha status in breast cancer," BMC Genomics 6:37 (2005) (13 pages).

Affymetrix Expression Probeset Details for HG-U133_PLUS_2:209083_AT, <www.affymetrix.com/analysis/netaffx/fullrecord.affx?pk=HG-U133_PLUS_2:209083_AT>, retrieved Nov. 27, 2018 (4 pages).

Agrawal et al., "Long-term effect of fulvestrant on hormone receptors and proliferation marker in breast cancer," EJC Supplements. 8(3):111 (2010).

Baker, "The central role of receiver operating characteristic (ROC) curves in evaluating tests for the early detection of cancer," J Natl Cancer Inst. 95(7):511-5 (2003).

Benner et al., "Evolution, language and analogy in functional genomics," Trends Genet. 17(7):414-8 (2001).

Bild et al., "Oncogenic pathway signatures in human cancers as a guide to targeted therapies," Nature. 439(7074):353-7 (2006).

Boulikas, "Clinical overview on Lipoplatin™: a successful liposomal formulation of cisplatin," Expert Opin Investig Drugs. 18(8):1197-218 (2009) (23 pages).

Buhl et al., "A genetic response profile to predict efficacy of adjuvant 5-FU in colon cancer," Ann Oncol. 25(Suppl. 4):iv167-209 (2014) (1 page).

Casagrande et al., "Preclinical Activity of the Liposomal Cisplatin Lipoplatin in Ovarian Cancer," Clin Cancer Res. 20(21):5496-5506 (12 pages).

Castelli et al., "In silico analysis of microRNAS targeting the HLA-G 3' untranslated region alleles and haplotypes," Hum Immunol. 70(12):1020-5 (2009).

Chow et al., "Increased expression of annexin I is associated with drug-resistance in nasopharyngeal carcinoma and other solid tumors," Proteomics Clin Appl. 3(6):654-62 (2009).

(56) References Cited

OTHER PUBLICATIONS

Communication pursuant to Article 94(3) EPC for European Application No. 11741685.9, dated May 19, 2014 (6 pages).
Communication pursuant to Rule 94(3) EPC for European Application No. 11741685.9, dated Jul. 24, 2015 (7 pages).
Communication pursuant to Rules 161(1) and 162 EPC for European Application No. 11741685.9, dated Dec. 6, 2012 (2 pages).
Communication pursuant to Article 164(2)(b) and Article 94(3) EPC for European Application No. 15820250.7, dated Jun. 6, 2019 (17 pages).
Dahlén et al., "Activation of the GLI oncogene through fusion with the beta-actin gene (ACTB) in a group of distinctive pericytic neoplasms: pericytoma with t(7;12)," Am J Pathol. 164(5):1645-53 (2004).
De Jonge et al., "Early cessation of the clinical development of LiPlaCis, a liposomal cisplatin formulation," Eur J Cancer. 46(16):3016-3021 (2010) (6 pages).
Dermer, "Another anniversary for the war on cancer," Bio/Technology. 12:320 (1994).
Di Lisio, "MicroRNA expression in B-cell lymphomas," Doctoral Thesis, Facultad de Ciencias, Departamento de Biología Molecular, Universidad Autónoma de Madrid (2012) (223 pages).
Elstrom et al., "Response to second-line therapy defines the potential for cure in patients with recurrent diffuse large B-cell lymphoma: implications for the development of novel therapeutic strategies," Clin Lymphoma Myeloma Leuk. 10(3):192-6 (2010).
English Translation of Decision / Order of Hearing of the Patent Application for Indian Patent Application No. 4565/KOLNP/2010, dated Sep. 8, 2017 (1 page).
English Translation of Office Action for Chinese Patent Application No. 200680052220.2 dated Feb. 5, 2013 (9 pages).
English translation of Office Action for Chinese Patent Application No. 201280038428.4, dated Jan. 23, 2015 (15 pages).
English translation of Second Office Action for Chinese Patent Application No. 201280038428.4, dated Sep. 15, 2015 (10 pages).
EPO Communication pursuant to Article 94(3) EPC for European Patent Application No. 12725624.6, dated Dec. 23, 2014 (6 pages).
EPO Communication Pursuant to Article 94(3) for European Application No. 12725624.6, dated Jul. 2, 2015 (4 pages).
EPO Communication Pursuant to Rules 161(1) and 162 EPC for European Application No. 12725624.6 dated Jan. 29, 2014 (2 pages).
Etter et al., "The combination of chemotherapy and intraperitoneal MegaFas Ligand improves treatment of ovarian carcinoma," Gynecol Oncol. 107(1):14-21 (2007).
Examination Report for Australian Patent Application No. 2011246976, dated Aug. 19, 2015 (3 pages).
Extended European Search Report for European Patent Application No. 17193243.7, dated Feb. 2, 2018 (12 pages).
Extended European Search Report for European Patent Application No. 17211034.8, dated May 22, 2018 (13 pages).
Extended European Search Report for European Application No. 18172585.4, dated Oct. 9, 2018 (7 pages).
Extended European Search Report for European Patent Application No. 19154186.1, dated Jun. 7, 2019 (9 pages).
Fournier et al., "Gene expression signature in organized and growth-arrested mammary acini predicts good outcome in breast cancer," Cancer Res. 66(14):7095-7102 (2006).
Friis-Hansen et al., "Mir-449 inhibits growth of gastric cancer cells partly by inhibiting the expression of met and amphiregulin," Gastroenterology. 136(5):A-165 (2009) (1 page).
Fumagalli et al., "Oral vinorelbine and capecitabine plus bevacizumab in recurrent inflammatory breast cancer: gene profiling and response to treatment," Thirty-Third Annual CTRC-AACR San Antonio Breast Cancer Symposium, Dec. 8-12, San Antonio, TX. Cancer Res. 70(24 Suppl.): Abstract P6-12-06 (2010) (4 pages).
Gallardo et al., "miR-34a as a prognostic marker of relapse in surgically resected non-small-cell lung cancer," Carcinogenesis. 30(11):1903-9 (2009).

Genbank Accession No. AY889152.1. Retrieved on Mar. 5, 2013 (2 pages).
GenBank Accession No. HC040507.1: Sequence 486 from Patent EP2112235 (1 page).
Gerspach et al., "Therapeutic targeting of CD95 and the TRAIL death receptors," Recent Pat Anticancer Drug Discov. 6(3):294-310 (2011).
Greaney et al., "APO010 kills haematological tumour cells while having no effect on the repopulating function of haematopoietic progenitor cells," Bone Marrow Transplant. 37(1):S105 (2006).
Grimm et al., "Drugs interfering with apoptosis in breast cancer," Curr Pharm Des. 17(3):272-83 (2011).
Invitation to file search results or a statement of non-availability pursuant to Rule 70b(1) EPC for European Application No. 11741685.9, dated Jul. 22, 2013 (1 page).
Invitation to Pay Additional Fees for International Application No. PCT/IB2015/002055, dated Mar. 29, 2016 (12 pages).
International Preliminary Report on Patentability for International Application No. PCT/IB2011/001405, dated Oct. 30, 2012 (13 pages).
International Preliminary Report on Patentability and Written Opinion of the International Searching Authority for International Application No. PCT/EP2012/002332 dated Dec. 2, 2013 (11 pages).
International Preliminary Report on Patentability and Written Opinion of the Searching Authority for International Patent Application No. PCT/IB2006/004048 dated Jun. 4, 2008 (10 pages).
International Preliminary Report on Patentability and Written Opinion of the Searching Authority for International Patent Application No. PCT/EP2008/003789 dated Nov. 17, 2009 (9 pages).
International Preliminary Report on Patentability issued for International Application No. PCT/EP2014/052236, dated Dec. 8, 2015 (1 page).
International Preliminary Report on Patentability and Written Opinion for International Patent Application No. PCT/IB2015/002055, dated Mar. 28, 2017 (14 pages).
International Search Report and Written Opinion for International Application No. PCT/EP2014/052236, dated Jul. 9, 2014 (21 pages).
International Search Report for International Application No. PCT/IB2011/001405, dated Apr. 19, 2012 (7 pages).
International Search Report for International Patent Application No. PCT/EP2012/002332, dated Nov. 8, 2012 (7 pages).
International Search Report for International Patent Application No. PCT/EP2008/003789 dated Jan. 9, 2009 (5 pages).
International Search Report for International Application No. PCT/IB2006/004048 dated May 14, 2008 (5 pages).
International Search Report for International Patent Application No. PCT/IB2015/002055, dated Jun. 10, 2016 (10 pages).
Ioannidis et al., "Comprehensive analysis of blood cells and plasma identifies tissue-specific miRNAs as potential novel circulating biomarkers in cattle," BMC Genomics. 19(1):243 (2018) (11 pages).
Juncker-Jensen et al., "Insulin-like growth factor binding protein 2 is a marker for antiestrogen resistant human breast cancer cell lines but is not a major growth regulator," Growth Horm IGF Res. 16(4):224-39 (2006).
Knudsen et al., "Development and validation of a gene expression score that predicts response to fulvestrant in breast cancer patients," PLoS One. 9(2):e87415 (2014) (12 pages).
Koeppel et al., "Irofulven cytotoxicity depends on transcription-coupled nucleotide excision repair and is correlated with XPG expression in solid tumor cells," Clin Cancer Res. 10(16):5604-13 (2004) (11 pages).
Kornmann et al., "Thymidylate synthase and dihydropyrimidine dehydrogenase mRNA expression levels: predictors for survival in colorectal cancer patients receiving adjuvant 5-fluorouracil," Clinical Cancer Res. 9(11):4116-24 (2003).
Kuter et al., "Dose-dependent change in biomarkers during neoadjuvant endocrine therapy with fulvestrant: results from NEWEST, a randomized Phase II study," Breast Cancer Res Treat. 133(1):237-46 (2012).
Lee et al., "Cancer pharmacogenomics: powerful tools in cancer chemotherapy and drug development," Oncologist. 10(2):104-11 (2005) (9 pages).

(56) References Cited

OTHER PUBLICATIONS

Li et al., "Intronic microRNA: discovery and biological implications," DNA Cell Biol. 26(4):195-207 (2007).
Li et al., "Selection of optimal oligonucleotide probes for microarrays using multiple criteria, global alignment and parameter estimation," Nucleic Acids Res. 33(19):6114-23 (2005).
Liang et al., "Caspase-mediated apoptosis and caspase-independent cell death induced by irofulven in prostate cancer cells," Mol Cancer Ther. 3(11):1385-96 (2004) (13 pages).
Liang et al., "Characterization of microRNA expression profiles in normal human tissues," BMC Genomics. 8(166):1-20 (2007).
López et al., Chapter 11: MicroRNAs in Lymphoma, *MicroRNAs in Cancer Translational Research*. W.C.S. Cho (ed.), 239-67 (2011).
McCune et al., "Prognosis of hormone-dependent breast cancers: implications of the presence of dysfunctional transcriptional networks activated by insulin via the immune transcription factor T-bet," Cancer Res. 70(2):685-96 (2010).
Medinger et al., "Gene-expression Profiling in Patients with Plasma Cell Myeloma Treated with Novel Agents," Cancer Genomics Proteomics. 13(4):275-9 (2016).
Michels, "The promises and challenges of epigenetic epidemiology," Exp Gerontol. 45(4):297-301 (2010).
Mizutani et al., "Significance of orotate phosphoribosyltransferase activity in renal cell carcinoma," J Urol. 171(2 Pt 1):605-10 (2004).
Murakami et al., "Cellular components that functionally interact with signaling phospholipase A(2)s," Biochim Biophys Acta. 1488(1-2):159-66 (2000).
Nair et al., "A simple practice guide for dose conversion between animals and human," J Basic Clin Pharm. 7(2):27-31 (2016).
Narita et al., "Lower expression of activating transcription factors 3 and 4 correlates with shorter progression-free survival in multiple myeloma patients receiving bortezomib plus dexamethasone therapy," Blood Cancer J. 5:e373 (2015) (8 pages).
NCode™ Multi-Species miRNA Microarray Probe Set, Version 2.0 (Cat. # MIRMPS2-01 ), retrieved from <www.invitrogen.com/site/us/en/home/Products-and-Services/Applications/epigenetics-noncoding-rna-research/miRNA-Profiling-/miRNA-Probe-Set-Files.html> (2009) (21 pages).
Nielsen et al., "Design of oligonucleotides for microarrays and perspectives for design of multi-transcriptome arrays," Nucleic Acids Res. 31(13):3491-6 (2003).
NIH DailyMed for Fluorouracil Injection, USP, revised May 2010, retrieved Jan. 29, 2019 (2010) (8 pages).
Nikas et al., "Prognosis of treatment response (pathological complete response) in breast cancer," Biomark Insights. 7:59-70 (2012).
Ocio et al., "The Activation of Fas Receptor by APO010, a Recombinant Form of Fas Ligand, Induces In Vitro and In Vivo Antimyeloma Activity," Blood. 110(11):1515 (2007) (4 pages) (Abstract Only).
Okumura et al., "Correlation between chemosensitivity and mRNA expression level of 5-fluorouracil-related metabolic enzymes during liver metastasis of colorectal cancer," Oncol Rep. 15(4):875-82 (2006).
"Oncology Venture presents LiPlaCis on AACR in New Orleans," Press release issued by Oncology Venture Sweden AB, Hoersholm, Denmark, Mar. 4, 2016 (2 pages).
Ooyama et al., "Gene expression analysis using human cancer xenografts to identify novel predictive marker genes for the efficacy of 5-fluorouracil-based drugs," Cancer Sci. 97(6):510-22 (2006).
Østrem et al., "Secretory phospholipase $A_2$ responsive liposomes exhibit a potent anti-neoplastic effect in vitro, but induce unforeseen severe toxicity in vivo," J Control Release. 262: 212-221 (2017).
Paul et al., "Impact of miRNA deregulation on mRNA expression profiles in response to environmental toxicant, nonylphenol," Mol Cell Toxicol. 7:259-69 (2011).
"Phase I/II Study to Evaluate the Safety and Tolerability of LiPlaCis in Patients With Advanced or Refractory Tumours (LiPlaCis)", U.S. National Library of Medicine, clinicaltrials.gov/ct2/show/record/NCT01861496, accessed Jan. 9, 2020 (10 pages).

Pourhassan et al., "Revisiting the use of $sPLA_2$-sensitive liposomes in cancer therapy," J Control Release. 261:163-173 (2017).
Pradervand et al., "Concordance among digital gene expression, microarrays, and qPCR when measuring differential expression of microRNAs," Biotechniques. 48(3):219-222 (2010).
Reid et al., "Circulating microRNAs: Association with disease and potential use as biomarkers," Crit Rev Oncol Hematol. 80(2):193-208 (2011).
Rouillard et al., "OligoArray 2.0: design of oligonucleotide probes for DNA microarrays using a thermodynamic approach," Nucleic Acids Res. 31(12):3057-62 (2003).
Saito-Hisaminato et al., "Genome-wide profiling of gene expression in 29 normal human tissues with a cDNA microarray," DNA Res. 9(2):35-45 (2002).
"Saline," *Churchill Livingstone's Dictionary of Nursing*, www.credoreference.com/entry/ehscldictnursing/saline (2006) (1 page).
Senzer et al., "Irofulven demonstrates clinical activity against metastatic hormone-refractory prostate cancer in a phase 2 single-agent trial," Am J Clin Oncol. 28(1):36-42 (2005).
Slonim, "From patterns to pathways: gene expression data analysis comes of age," Nat Genet. 32 Suppl:502-8 (2002).
Suresh et al., "Resistance/response molecular signature for oral tongue squamous cell carcinoma," Dis Markers. 32(1):51-64 (2012).
Vangsted et al., "APO010 sensitivity in relapsed multiple myeloma patients," Annals of Oncol. 27(Supplement 6): vi15-vi42 (2016) (2 pages) (Abstract only).
Van't Veer et al., "Gene expression profiling predicts clinical outcome of breast cancer," Nature. 415(6871):530-6 (2002).
Verbrugge et al., "Combining radiotherapy with APO010 in cancer treatment," Clin Cancer Res. 15(6):2031-8 (2009) (9 pages).
Wang et al., "Independent Validation of a Model Using Cell Line Chemosensitivity to Predict Response to Therapy," J Natl Cancer Inst. 105(17): 1284-91 (2013).
Woynarowska et al., "Changes in prostate-specific antigen (PSA) level correlate with growth inhibition of prostate cancer cells treated in vitro with a novel anticancer drug, irofulven," Invest New Drugs. 19(4):283-91 (2001).
Xu et al., "[Association of miRNAs expression profiles with prognosis and relapse in childhood acute lymphoblastic leukemia]," Zhonghua Xue Ye Xue Za Zhi. 32(3):178-81 (Abstract only) (2011).
Yang et al., "The role of microRNA in human lung squamous cell carcinoma," Cancer Genet Cytogenet. 200(2):127-33 (2010).
Yin, "Screening of laryngeal carcinoma multidrug resistance-associated genes and study on reversion by Chinese herbs," China Doctoral Dissertations Full-text Database, Division of Medical and Hygiene Technology. 8:E072-85 (2010) (3 pages) (Abstract only).
Zhang et al., "MicroRNA-650 targets ING4 to promote gastric cancer tumorigenicity," Biochem Biophys Res Commun. 395(2):275-280 (2010).
Buhl et al., "Molecular prediction of adjuvant cisplatin efficacy in Non-Small Cell Lung Cancer (NSCLC)—validation in two independent cohorts," PLoS One.13(3): e0194609 (2018) (12 pages).
Zhu et al., "Secretory phospholipase A2 responsive liposomes," J Pharm Sci. 100(8):3146-3159 (2011).
Buckland et al., "Bacterial cell membrane hydrolysis by secreted phospholipases A(2): a major physiological role of human group IIa sPLA(2) involving both bacterial cell wall penetration and interfacial catalysis," Biochim Biophys Acta 1484(2-3):195-206 (2000).
Buckland et al., "Anionic phospholipids, interfacial binding and the regulation of cell functions," Biochim Biophys Acta. 1483(2):199-216 (2000).
Xu et al., "The effect of cholesterol domains on PEGylated liposomal gene delivery in vitro", Ther Deliv. 2(4):451-60 (2011).
Bentz et al., "Temperature dependence of divalent cation induced fusion of phosphatidylserine liposomes: evaluation of the kinetic rate constants," Biochemistry. 24(4):1064-72 (1985).
Chonn et al., "The role of surface charge in the activation of the classical and alternative pathways of complement by liposomes," J Immunol. 146(12):4234-41 (1991).
Düzgünes et al., "Calcium- and magnesium-induced fusion of mixed phosphatidylserine/phosphatidylcholine vesicles: effect of ion binding," J Membr Biol. 59(2):115-25 (1981).

(56) References Cited

OTHER PUBLICATIONS

Epand et al., "Effect of electrostatic repulsion on the morphology and thermotropic transitions of anionic phospholipids," FEBS Lett. 209(2):257-60 (1986).

Jerremalm et al., "Alkaline hydrolysis of oxaliplatin—isolation and identification of the oxalato monodentate intermediate," J Pharm Sci. 91(10):2116-21 (2002).

Jerremalm et al., "Hydrolysis of oxaliplatin—evaluation of the acid dissociation constant for the oxalato monodentate complex," J Pharm Sci. 92(2):436-8 (2003).

Jerremalm et al., "Oxaliplatin degradation in the presence of chloride: identification and cytotoxicity of the monochloro monooxalato complex," Pharm Res. 21(5):891-4 (2004).

Jerremalm et al., "Oxaliplatin degradation in the presence of important biological sulphur-containing compounds and plasma ultrafiltrate," Eur J Pharm Sci. 28(4):278-83 (2006).

Jørgensen et al., "Biophysical mechanisms of phospholipase A2 activation and their use in liposome-based drug delivery," FEBS Lett. 531(1): 23-7 (2002).

Kenworthy et al., "Range and magnitude of the steric pressure between bilayers containing phospholipids with covalently attached poly(ethylene glycol)," Biophys J. 68(5):1921-36 (1995).

Kenworthy et al., "Structure and phase behavior of lipid suspensions containing phospholipids with covalently attached poly(ethylene glycol)," Biophys J. 68(5):1903-20 (1995).

Leung et al., "Phospholipase A2 group IIA expression in gastric adenocarcinoma is associated with prolonged survival and less frequent metastasis," Proc Natl Acad Sci U S A. 99(25):16203-8 (2002).

Logisz et al., "Effect of salt concentration on membrane lysis pressure," Biochim Biophys Acta. 1717(2):104-8 (2005).

Narenji et al., "Effect of Charge on Separation of Liposomes upon Stagnation," Iran J Pharm Res. 16(2):423-431 (2017).

Needham et al., "Exchange of monooleoylphosphatidylcholine as monomer and micelle with membranes containing poly(ethylene glycol)-lipid," Biophys J. 73(5):2615-29 (1997).

Praml et al., "Secretory type II phospholipase A2 (PLA2G2A) expression status in colorectal carcinoma derived cell lines and in normal colonic mucosa," Oncogene. 17(15):2009-12 (1998).

Shoemaker et al., "Calcium modulates the mechanical properties of anionic phospholipid membranes," J Colloid Interface Sci. 266(2):314-21 (2003).

Szebeni et al., "Liposome-induced complement activation and related cardiopulmonary distress in pigs: factors promoting reactogenicity of Doxil and AmBisome," Nanomedicine. 8(2):176-84 (2012).

Stathopoulos, George P., "Liposomal cisplatin: a new cisplatin formulation," Anticancer Drugs. 21(8):732-6 (2010). (Abstract only).

Quach et al., "Secretory phospholipase A2 enzymes as pharmacological targets for treatment of disease," Biochem Pharmacol. 90(4):338-48 (2014).

* cited by examiner

Figure 15

| Subject No. | Gender | Age | Diagnosis | History of Cisplatin | Dose, mg/subject | 1st Cycle | 2nd Cycle | 3rd Cycle | Comments |
|---|---|---|---|---|---|---|---|---|---|
| 1 | F | 63 | Breast Cancer | No | 10 | OK | OK | OK | PD |
| 2 | F | 49 | Melanoma | No | 10 | Allergic reaction, grade 2-3 | Allergic Reaction, grade 3, DLT | Not done | Off study after 2 cycles |
| 3 | F | 75 | Adenoid Cystic Carcinoma | No | 10 | OK | OK | OK | PD after 15 cycles |
| 4 | M | 51 | Oesophargyeal Cancer | No | 10 | OK | OK | OK | PD after 3 cycles |
| 5 | M | 61 | Prostate Cancer | No | 10 | Allergic reaction grade 2 | OK | OK | PD after 6 cycles |
| 6 | F | 44 | Oropharyngeal cancer | No | 10 | OK | OK | Not done | Off study after 2 cycles due to PD |
| 7 | F | 39 | Parotic Cancer | ? | 20 | OK | OK | OK | PD after 3 cycles |
| 8 | M | 56 | Urothelial-cell Cancer | ? | 20 | OK | OK | OK | PD after 3 cycles |
| 9 | M | 64 | Parotic Cancer | ? | 20 | OK | OK | OK | PD after 6 cycles |
| 10 | M | 66 | Melanoma | ? | 40 | OK | OK | Not done | PD after 2 cycles |
| 11 | M | 71 | Prostate Cancer | ? | 40 | OK | OK | Not done | Off-study after 2 cycles. |
| 12 | F | 45 | Breast Cancer | ? | 40 | OK | Not done | Not done | Off study after first cycle. PD |
| 13 | M | 62 | Urothelial-cell Cancer | ? | 80 | OK | OK | OK | |
| 14 | F | 50 | CUP | ? | 80 | Allergic reaction grade 2 | Allergic reaction grade 3 | Not done | Off study after 2 cycles |
| 15 | M | 53 | Hypopharyngeal cancer | ? | 80 | OK | OK | Pending | |

Figure 16A

| Pt. Nr. | Dose | Sex | Age | Tumor | Cycle | Day | WBC | ANC | PLT | Hgb | Nau | Vom | Dia | Oral | Renal | Fever | Neuro | Fatigue | Other | DLT | Response |
|---|---|---|---|---|---|---|---|---|---|---|---|---|---|---|---|---|---|---|---|---|---|
| 5001 | 10 mg | F | 63 | breast | 0 | | 1 | | | | | | | | | | | | ASAT 2, ALAT 2, LDH 1 | | |
| | | | | | 1 | | 1 | | 1 | | | | | | | | | | skin 1 (dry desquamation), ASAT 2, ALAT 2 | | |
| | | | | | 2 | | 1 | | 1 | | | | | | | | | | AST 2, ALT 2 | | |
| | | | | | 3 | | | | | | | | | | | | | | AST 1, ALT 1, LDH 1 | | |
| | | | | | off | | | | | | | | | | | | | | | X | PD |
| 5002 | 10 mg | F | 49 | melanoma | 0 | | | | | | | | | | | | | | pain 1 | | |
| | | | | | 1 | | | | | | 1 | | | | | | | 2 | allergic reaction 3, rash 1, anorexia 1, AST 2, ALT 2, GGT 1 | | |
| | | | | | 2 | | | | | | | | | | | | | | allergic reaction 3 (despite pre-medication), medication stop | | |
| 5008 | 10 mg | F | 75 | adenoidcystic carcinoma | off | | | | | | | | | | | | | | | | |
| | | | | | 0 | | | | | | | | | | | | | | | | |
| | | | | | 1 | | | | | | | | | | | | | | GGT 1 | | |
| | | | | | 2 | | | | | | | | | | | | | | | | |
| | | | | | 3 | | | | | | | | | | | | | | AST 1, cholesterol 1 | | SD |
| | | | | | 4 | | | | | | | | | | | | | | GGT 1, hypercholesterol 1 | | |
| | | | | | 5 | | | | | | | | | | | | | | GGT 1, hypercholesterol 1 | | |
| | | | | | 6 | | | | | | | | | | | | | | hypercholesterol 1 | | SD |
| | | | | | 7 | | | | | | | | | | | | | | hypercholesterol 1 | | |
| | | | | | 8 | | | | | | | | | | | | | | hypercholesterol 1 | | |
| | | | | | 9 | | | | | | | | | | | | | | hypercholesterol 1, glucose 1 | | SD |
| | | | | | 10 | | | | | | | | | | | | | | hypercholesterol 1, glucose 1 | | |
| | | | | | 11 | | | | | | | | | | | | | | hypercholesterol 1 | | |

MEDICAL USE OF SPLA2 HYDROLYSABLE
LIPOSOMES

FIELD OF THE INVENTION

The present invention relates to liposomal drug delivery systems and their use in therapy.

BACKGROUND

Liposomes for Drug Delivery

Liposomes are microscopic spheres which were developed as drug delivery vehicles/systems in the 1980s. The first liposome-based pharmaceuticals were approved for commercial use in the 1990s.

Liposomes have three distinct compartments that can be used to carry various compounds such as drugs: The interior aqueous compartment; the hydrophobic bilayer; and the polar inter-phase of the inner and outer leaflet. Depending on the chemical nature of the compound to be encapsulated it will be localised to either of the compartments.

Liposomes are considered a promising drug delivery system since they passively target tumor tissue by using the pathophysiological characteristics of solid tumors such as hyperplasia and increased vascular permeability but also a defect in lymphatic drainage. These features facilitate extravasation of nanoparticles and the liposomes can be retained in the tissue for longer time due to the enhanced permeability and retention effect (EPR).

The property of liposomes as drug delivery vehicles is crucially dependent on their surface charge, permeability, solubility, stability etc. which is significantly influenced by the lipids comprised in the liposome composition. In addition, the drug to be encapsulated in the liposome may need further requirements to be considered in preparing a stable liposome formulation.

Considerations regarding safety and drug efficacy require that liposome formulations maintain their properties, i.e. remain stable, from the time of preparation until administration. Furthermore, it is desirable that such formulations are intact during the transport in the treated subject until they reach the target site where the drug is specifically released.

Therapeutic use of negatively charged liposomes may induce non-IgE-mediated hypersensitivity reactions seen in patients treated with liposomal products. These adverse reactions are thought to be a result of anaphylatoxin production through complement activation.

Repeated dosing of PEGylated liposomal formulations has in some cases resulted in an Accelerated Blood Clearance (ABC-phenomenon) leading to a fast clearance from the bloodstream and corresponding increased accumulation in liver and spleen when compared to the first dose. The ABC-phenomenon may cause unintended release of encapsulated compound in organs having accumulated liposomes. Moreover, the ABC-phenomenon is typically non-desired as it may prevent the liposomes from accumulating at intended sites.

Various targeting strategies for liposomes have been described, e.g. conjugation to cell specific ligands such as antibodies.

sPLA2 Hydrolysable Liposomes

Another approach has been suggested based upon elevated levels of secretory phospholipase A2 (sPLA2) in cancerous tissue and also at sites of inflammation. The basic idea is that liposomes can be prepared which are hydrolysable by sPLA2 and that hydrolysis by sPLA2 leads to release of the drug encapsulated within the liposome. Moreover, the products of sPLA2 hydrolysis, a lysolipid and a fatty acid act as permeabilizers of cell membranes leading to increased cell uptake of the drug. Since sPLA2 levels are elevated in the cancerous tissues and at sites of inflammation, sPLA2 activated liposomes may be used to preferentially deliver encapsulated drugs to such sites.

A number of documents have described sPLA2 activated liposomes, but therapeutic applications have so far not been described.

WO0158910 described sPLA2 activated liposomes comprising prodrugs of mono-ether lyso-phospholipids. This document also described encapsulation of additional bioactive compounds. However, no therapeutic use of the described liposomes was disclosed.

WO0176555 suggested the use of a lipid-based drug delivery system for treatment of diseases or conditions associated with a localized increase in extracellular sPLA2 in cutaneous or subcutaneous tissue of a mammal, for administration of a prodrug of an ether-lysolipid that is activated by sPLA2. The system further comprised a so-called edge active compound. This document did not disclose topical application to a mammal such as a human. Hence no therapeutic use of the described liposomes was disclosed.

WO0176556 suggested the use of a lipid-based drug delivery system for treatment or prevention of a parasitic infection selected from Leishmaniasis, Tryponosomiasis, malaria, Entaboeba, Histolyticasis and "Oriental liver fluke chlomorchis sinensis", wherein the system comprised prodrugs in the form of lipid derivatives that are activated by sPLA2. The liposomes may contain an additional bioactive compound. No actual treatment of the mentioned infections was demonstrated nor was the liposomes administered to a mammal such as a human.

WO06048017 and WO07107161 did also describe sPLA2 activated liposomes, but without any disclosure of medical treatment.

Andresen et al, 2005a (Andresen T L, 2005) discussed triggered activation and release of liposomal prodrugs and drugs in cancer tissue by sPLA2. Among others, the authors disclosed data from an experiment showing inhibition of tumour growth in the MT-3 breast xenograft mouse model. Cisplatin encapsulated in sPLA2 degradable liposomes (DSPC/DSPG/DSPE-PEG2000, no amounts of the individual lipids were given) showed increased inhibition of tumour growth as compared to an equivalent amount of free cisplatin. The authors also noted that in in vitro experiments, the sPLA2 degradable liposomes loaded with cisplatin were more cytotoxic than free cisplatin possibly due to an additive membrane perturbing effect of the hydrolysis products, lysolipid and fatty acids. This effect might be useful for facilitating transmembrane diffusion of cisplatin into intracellular target sites. Whether this effect can lead to adverse side effects of sPLA2 activated liposomes was not discussed.

Andresen et al, 2005b (Andresen T L J. S., 2005) also disclosed data from an experiment showing inhibition of tumour growth in the MT-3 breast xenograft mouse model.

Even in view of the references discussed above, it is unclear whether sPLA2 activated liposomes can be used therapeutically. They may e.g. be rapidly cleared by the cells of the RES because of their typically negative charge. They may also simply be too leaky for therapeutic use. Another very unpredictable parameter is toxicity of the sPLA2 liposomes. As mentioned, the products of sPLA2 mediated hydrolysis, lysolipids and fatty acids, may lead to unintended side effects e.g. through permeabilization of cell membranes. Moreover, drug release at unintended sites may occur if sPLA2 is present at increased levels at sites other than in tumours. Such unintended drug release may have detrimental consequences and prevent therapeutic use of sPLA2 activated liposomes. Drug release at unintended sites may be caused by unanticipated elevated sPLA2 levels at such sites.

The therapeutically use of negatively charge liposomes could involve non-IgE-mediated hypersensitivity reactions seen in patients treated with liposomal products. These reactions are thought to be a result of anaphylatoxin production through complement activation.

Repeated dosing of PEGylated liposomal formulations has in some cases resulted in an Accelerated Blood Clearance (ABC-phenomenon) leading to a fast clearance from the bloodstream and corresponding increased accumulation in liver and spleen when compared to the first dose. The ABC-phenomenon may course unintended release of encapsulated compound in organs having accumulated liposomes.

Treatment Using Cisplatin

Free cisplatin formulations have some serious side effects. The most important are listed below:

Nephrotoxicity—The major dose-limiting toxicity of cisplatin is dose-related and cumulative renal insufficiency. The administration of cis-platin using a 6- to 8-hour infusion with intravenous hydration has been used to reduce nephrotoxicity. However, renal toxicity still can occur after utilization of these procedures.

Ototoxicity—Ototoxicity has been observed in up to 31% of patients treated with a single dose of cisplatin 50 mg/m2, and is manifested by tinnitus and/or hearing loss in the high frequency range (4,000 to 8,000 Hz). Ototoxic effects may be related to the peak plasma concentration of cisplatin.

Hematologic—Myelosuppression occurs in 25% to 30% of patients treated with cisplatin. Leukopenia and thrombocytopenia are more pronounced at higher doses (>50 mg/m2). Anemia occurs at approximately the same frequency as leukopenia and thrombocytopenia Gastrointestinal—Marked nausea and vomiting occur in almost all patients treated with cisplatin, and are occasionally so severe that the drug must be discontinued. Nausea and vomiting usually begin within 1 to 4 hours after treatment and last up to 24 hours.

Serum Electrolyte Disturbances—Hypomagnesemia, hypocalcemia, hyponatremia, hypokalemia, and hypophosphatemia have been reported to occur in patients treated with cisplatin and are probably related to renal tubular damage.

Neurotoxicity—Neurotoxicity is usually characterized by peripheral neuropathies. The neuropathies usually occur after prolonged therapy (4 to 7 months); however, neurologic symptoms have been reported to occur after a single dose.

Hepatotoxicity—Transient elevations of liver enzymes, especially SGOT, as well as bilirubin, have been reported to be associated with cisplatin administration at the recommended doses.

Thus, treatment using free cisplatin has a number of potential side effects and there is a need for cisplatin formulations with a reduced risk of side effects.

SUMMARY OF THE INVENTION

In a first aspect, the present invention provides sPLAs hydrolysable liposomes for medical use. The sPLA2 hydrolysable liposomes preferably comprise a therapeutic agent such as a small molecule antitumor agent.

Other aspects of the present invention relates to methods of reducing the side effects of therapeutic agents, e.g. reducing nephrotoxicity, neurotoxicity and gastrointestinal toxicity of a therapeutic agent.

Yet another aspect of the present invention relate to methods of prolonging the therapeutic effect of a therapeutic agent.

Figure 1:
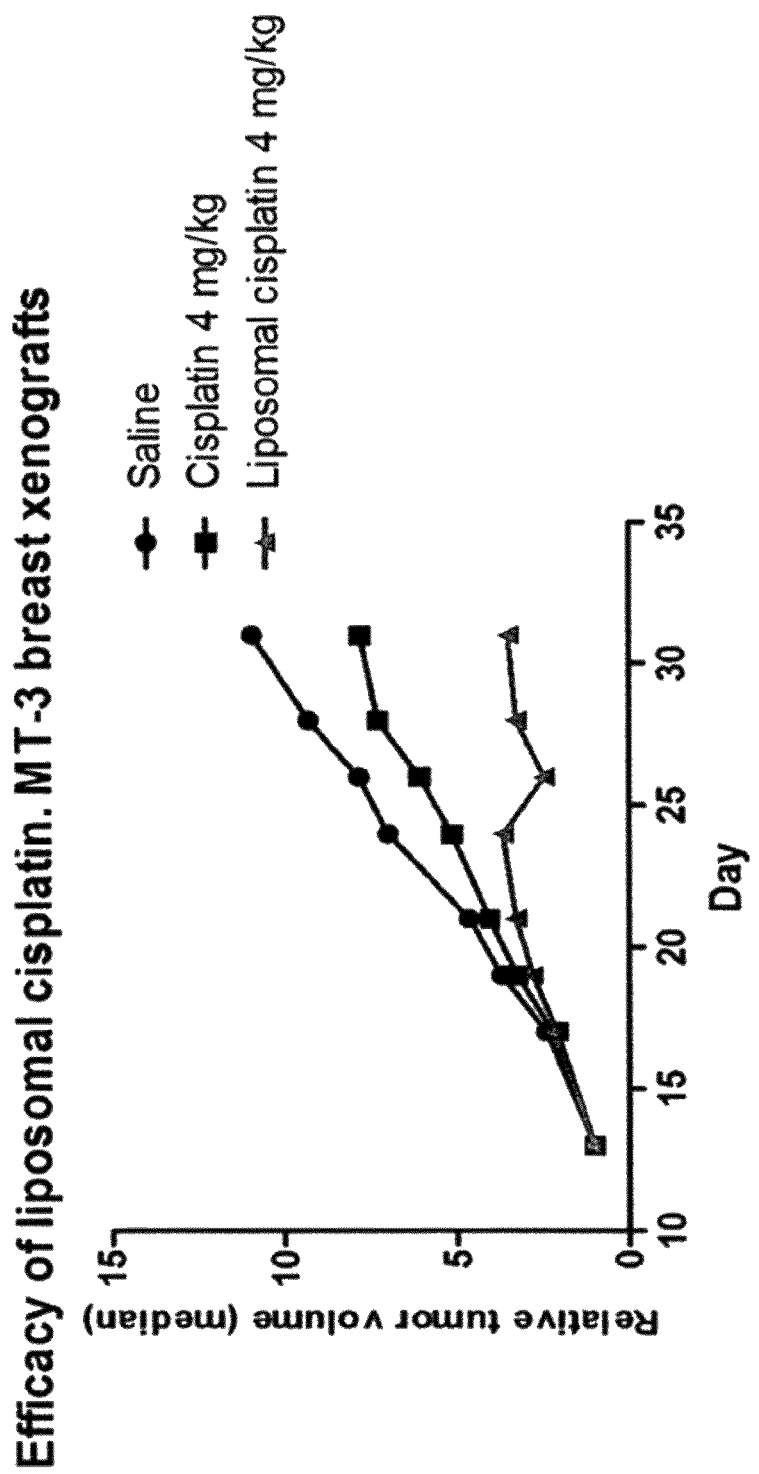
FIG. 1.

Efficacy of LiPlaCis towards MT-3 (human breast carcinoma) xenografts. Nude mice with exponentially growing tumors were treated once weekly with 4 mg/kg cisplatin or LiPlaCis. The control group was treated with (saline). The cisplatin and saline-treated groups received three injections whereas the LiPlaCis-treated mice only received two injections due to toxicity. See example 2 for details.

FIG. 2.

Rats (BrlHan:WIST@Mol(GALAS)) (3 rats/treatment) were injected with 3 mg/kg cisplatin or LiPlacis and blood was withdrawn at the indicated time points. After acid digestion, the plasma fraction was analyzed for platinum content using ICP-MS. See example 2 for details.

FIGS. 3-7

Pharmacokinetics and biodistribution in nude mice bearing MT-3 xenografts. Nude mice (3 mice/timepoint/treatment) with exponentially growing MT-3 tumors were injected with a single dose of cisplatin or LiPlaCis (3 mg/kg). After blood withdrawal, the mice were sacrificed at the indicated time points and tumors and organs were dissected, washed and snap frozen. After acid digestion, the platinum content was measured by ICP-MS. See example 4 for details.

FIGS. 8-11

Cisplatin concentration in blood as a function of time after administration of LiPlaCis. See example 6 for details.

FIGS. 12-14

Cisplatin concentration in blood as a function of administered amount of LiPlaCis. See example 6 for details.

FIG. 15

Summary of phase 1 data. See example 6 for details.

FIGS. 16A-16E

Detailed phase 1 data. WBC WBC~white blood cells, ANC~absolute neutrophil count, PLT~platelets, Hgb~hemoglobin, Nau~Nausea, Vom~vomiting, Dia~diarrhea. See example 6 for details.

DISCLOSURE OF THE INVENTION

The present inventors have carried out in vivo studies with sPLA2 hydrolysable liposomes (also herein termed sPLA2 activated liposomes). When sPLA2 hydrolysable liposomes loaded with cisplatin (herein also termed LiPlaCis) was administered to tumor mice models, an increased efficacy as compared to administration of free cisplatin was often observed. However, increased efficacy was also often entailed by increased toxicity leading to death of mice.

Nonetheless, the present inventors initiated a phase 1 dose escalation trial of cisplatin encapsulated in sPLA2 hydrolysable liposomes in patients with advanced or refractory tumors. The primary endpoint of the study was safety and tolerability of cisplatin encapsulated in sPLA2 hydrolysable liposomes (also termed LiPlaCis).

The main conclusions of the study were:

LiPlaCis has a tolerable tox profile at clinically relevant doses.

LiPlaCis enables administration of at least the same dose of cisplatin as administration of free cisplatin, which is surprising in view of non-clinical data.

LiPlaCis reduced nephrotoxicity as compared to administration of free cisplatin, which is typically dose limiting for cisplatin.

LiPlaCis reduced nausea and vomiting as compared to administration of free cisplatin The MTD (maximum tolerated dose) of LiPlaCis given every 3 weeks was determined to be above 80 mg per treatment cycle, which is surprising in view of the MTD predicted from animal experiments.

The RD (recommended dose) of LiPlaCis given every 3 weeks was determined to 80 mg per treatment cycle or higher.

LiPlaCis can be administrated without hydration, which is required for administration of free cisplatin. LiPlaCis can be administered on an outpatient basis.

In particular, LiPlaCis had good safety and tolerability profile compared to free cisplatin formulations in terms of nausea, diarrhea, vomiting, anemia, neuropathy, nephrotoxicity and ototoxicity.

Thus, the present invention has made medical use of sPLA2 hydrolysable liposomes available and in its broadest aspect provides a sPLA2 hydrolysable liposome for use in therapy, preferably treatment of humans.

sPLA2 Hydrolysable Liposomes sPLA2 hydrolysable liposomes for use in therapy according to the present invention are defined in more detail in the following embodiments. In its broadest embodiment, the term sPLA2 hydrolysable liposomes refer to liposomes that are hydrolysable under physiological conditions, particular in cancerous tissue.

Preferably, the sPLA2 hydrolysable liposomes comprises between 20% and 45% (mol/mol) of an anionic lipid. The content of anionic lipid affects important characteristics of the liposome, such as the rate of sPLA2 mediated lipid hydrolysis of the liposome and also the immune response toward the liposome.

As the content of anionic lipid increases, so does the rate of lipid hydrolysis by $sPLA_2$ (and the release of drug). It has been demonstrated that a reasonable rate of hydrolysis can be achieved by an anionic lipid content between 20% and 45%. Thus, in one embodiment, the content of anionic lipid is at least 20%. In another embodiment, the content of anionic lipid is no more than 45%. In yet another embodiment, the anionic lipid content of the liposome is selected from the group consisting of between 20% and 45%, between 25% and 45%, between 28% and 42%, between 30% and 40%, between 32% and 38% and between 34% and 36%.

As mentioned, also the immune response toward the liposomes is affected by the content of anionic lipid. Thus, the clearance rate of the liposome in the body may be reduced by keeping the content of the anionic lipid in the liposome below a certain level and the present inventors have recognized that the content of anionic lipid in the liposome can be used to strike a balance between hydrolysis rate of $sPLA_2$ and clearance by the reticuloendothelial system.

Preferably the anionic lipid is a phospholipid and preferably, the phospholipid is selected from the group consisting of PI (phosphatidyl inositol), PS (phosphatidyl serine), DPG (bisphosphatidyl glycerol), PA (phosphatidic acid), PEOH (phosphatidyl alcohol), and PG (phosphatidyl glycerol). More preferably, the anionic phospholipid is PG. Preferably, the lipids comprise stearoyl chains. Thus preferably PG is DSPG etc.

Hydrophilic Polymers

In a preferred embodiment, the sPLA2 hydrolysable liposome for use in the present invention further comprises a hydrophilic polymer selected from the group consisting of PEG [poly(ethylene glycol)], PAcM [poly(N-acryloylmorpholine)], PVP [poly(vinylpyrrolidone)], PLA [poly(lactide)], PG [poly(glycolide)], POZO [poly(2-methyl-2-oxazoline)], PVA [poly(vinyl alcohol)], HPMC (hydroxypropylmethylcellulose), PEO [poly(ethylene oxide)], chitosan [poly(D-glucosamine)], PAA [poly(aminoacid)], polyHEMA [Poly(2-hydroxyethylmethacrylate)] and co-polymers thereof.

Most preferably the polymer is PEG with a molecular weight between 100 Da and kDa. Particular preferred are PEG sizes of 2-5 kDa (PEG2000 to PEG5000), and most preferred is PEG2000.

The inclusion of polymers on liposomes is well known to the skilled artisan and can be used to increase the half-life of the liposomes in the bloodstream, presumably by reducing clearance by the reticuloendothelial system. Moreover, the inclusion of polymers affects sPLA2 hydrolysis.

Preferably, the polymer is conjugated to the head group of phospatidyl ethanolamine. Another option is conjugation to ceramide (even though this lipid is not hydrolyzable by $sPLA_2$). When the polymer is conjugated to phospatidyl ethanolamine, a negative charge is introduced and hence DSPE-PEG is regarded as an anionic lipid (contrary to DSPE which is regarded as a neutral lipid). The polymer-conjugated lipid is preferably present at an amount of at least 2%. More preferably, the amount is at least 5% and no more than 15% (mol/mol). Even more preferably, the amount of polymer-conjugated lipid is at least 3% and no more than 6%. Liposomes containing anionic phospholipids and % DSPE-PEG2000 have increased tendency to aggregate in the presence of calcium. This can usually be observed by formation of high viscous gel. Liposomes containing anionic phospholipids and >7.5% DSPE-PEG2000 causes the liposomes to sediment or phase separate.

Neutrally Charged Lipid Components in the Liposome

Preferably, the liposome to be used in the present invention also comprises an uncharged phospholipid selected from the group consisting of zwitterionic phospholipids comprising PC (phosphatidyl choline) and PE (phosphatidylethanolamine). Most preferably, the zwitterionic phospholipid is PC.

In contrast to anionic phospholipid, zwitterionic phospholipid serves as a charge neutral $sPLA_2$-hydrolyzable lipid component in the liposome. By combining zwitterionic- and anionic phospholipid in the same liposome, it is possible to adjust to a desired surface charge density which complies with both sufficiently high $sPLA_2$ hydrolysis and a low clearance rate in the blood.

The amount of zwitterionic phospholipid in the liposome is preferably between 40% and 75% and more preferably between 50 and 70%.

Preferably, the lipids (anionic lipids, neutral lipids and polymer conjugated lipids) comprise stearoyl chains). Thus preferably PG is DSPG, PE is preferably DSPE etc.

Ether-Phospholipids

Some or all of the phospholipids may be ether-phospholipids.

Thus, they may harbour an ether-bond instead of an ester-bond at the sn-1 position of the glycerol backbone of the phospholipid. When $sPLA_2$ hydrolyze this particular type of phospholipids, mono-ether lyso-phospholipids are produced and these are toxic to e.g. cancer cells. I.e. ether phospholipids may be seen as pro-drugs of mono-ether lyso-phospholipids and liposomes of the invention can be used to deliver such pro-drugs to the sPLA$_2$-enhanced environment of cancer cells, where the pro-drugs are activated by sPLA$_2$ hydrolysis. Ether-phospholipids have been described in EP 1254143 and WO 2006/048017, the contents of which are hereby incorporated by reference.

In one embodiment, the sPLA2 activated liposomes as used in the present invention does not comprise ether-phospolipids.

Other Pro-Drugs

The moiety released from the lipid by sPLA$_2$ to create a lysolipid may also be a drug. Thus, a liposome may comprise pro-drugs of mono-ether lysolipids, pro-drugs released from the lipid by sPLA$_2$ and other therapeutic agents, as further outlined below.

In one embodiment, the sPLA2 activated liposomes as used in the present invention does not comprise prodrugs released from the lipid by sPLA2.

Stabilizing Agent

The liposome may be stabilized by the inclusion of cholesterol as membrane component in the liposome. However, high amounts of cholesterol in the liposome have a negative effect on hydrolysis by PLA$_2$ and therefore it is preferred that the liposome comprises no more than 10% cholesterol. Even more preferably, the liposome comprises less than 1% cholesterol, less than 0.1% or does not comprise any cholesterol at all.

The alkyl chain length of the lipids comprising the liposome may be adjusted for optimal PLA$_2$ hydrolysis rate and minimum leakage of entrapped compound out of the liposome. Preferably, the alkyl chains are C18 or C16 saturated chains.

The liposomes to be used may be stabilized by exposure to divalent cations.

As described above, the liposomes may comprise pro-drugs of mono-ether lysolipids and/or of the moiety released from the lipid by sPLA$_2$ to create the lysolipid.

In a preferred embodiment, the liposomes comprise a bioactive compound such as a therapeutic agent (drug), which is not a pro-drug of mono-ether lysophospholipid or a mono-ether lysophospholipid. The liposome may also comprise pro-drugs of mono-ether lysophospholipid and a therapeutic agent. Preferred bioactive compounds are small molecules, peptides, proteins and nucleic acids such as plasmids and oligonucleotides. A preferred class of proteins is antibodies, more preferably monoclonal antibodies. Preferred oligonucleotides are aptamers, antisense oligonucleotides, microRNAs and siRNAs. A class of compounds of particular interest is small molecule antitumour agents such as anthracyclin derivatives, cisplatin, oxaliplatin, carboplatin, doxorubicin, paclitaxel, 5-fluoruracil, exisulind, cis-retinoic acid, suldinac sulphide, methotrexate, bleomycin and vincristine. A preferred subclass of antitumor agents is platinum based antitumor agents; cisplatin, oxaliplatin, picoplatin and carboplatin. Another class of compounds of particular interest is antibiotics and antifungals and yet another class is anti-inflammatory agents such as steroids and non-steroids.

The therapeutic agent may be located in the interior aqueous compartment; the hydrophobic bilayer; or the polar inter-phase of the inner and outer leaflet.

Preferably, the therapeutic agent is encapsulated in the liposome, i.e. present in the interior aqueous compartment.

In another embodiment, the liposome comprises a diagnostic agent. By "diagnostic agent" is meant an agent that supports the localisation of the target tissue and/or the diagnosis of the disease and/or condition. Non-limiting examples could be contrast agents, microparticles, radioactive agents, target specific agents such as e.g. agents that bind specifically to markers associated with the disease and/or condition, etc. It is clear to a skilled person that in some embodiments the invention relates to a liposome formulation wherein the liposome comprises at least one drug as well as a diagnostic agent.

Physical-Chemical Characteristics of the Liposomes of the Invention

The liposome can be unilamellar or multilamellar. Most preferably, the liposome is unilamellar. The diameter of the liposome should be between 50 and 400 nm, preferably between 80 and 160 nm and most preferable between 90 and 120 nm.

Preferably, the Poly Dispersity Index (PDI) of the liposomal formulation of the second aspect of the invention should not exceed 0.2 and more preferable is 0.10 or less. A PDI value in this range expresses a relatively narrow particle size-distribution in the formulation.

As will be clear from the above, it is preferred that at least one of the lipids comprising the liposome is a substrate for sPLA$_2$ when present in the liposome.

In one embodiment, the liposome comprises lipids which are hydrolysed by sPLA$_2$ at the sn-3 position instead of at the sn-2 position. Such unnatural lipids and liposomes comprising unnatural lipids have been disclosed in WO 2006/048017, the content of which is hereby incorporated by reference.

In a most preferred embodiment, the liposomes to be used in the present invention comprise 70% DSPC, 25% DSPG and 5% DSPE-PEG.

When the therapeutic agent is cisplatin, the interior of the liposomes preferably comprises 0.9% NaCl and the exterior buffer solution comprises 10 mM phosphate buffer at pH 6.5, 1 mM NaCl and 10% sucrose.

Medical Use

In a preferred embodiment, the sPLA2 hydrolysable liposome is administered by injection (parenteral administration) e.g. the subcutaneous, intramuscular, intra-peritoneal, intravenous, and intrathecal routes. A preferred route is intravenous administration in form of bolus injection or infusion.

As described above, the liposome may comprise various therapeutic agents. However, preferred agents are small molecule anti tumour agents (herein also termed antineoplastic agents, cytotoxic drugs or cytostatic drugs). Cisplatin is one of these compounds and the demonstration that cisplatin encapsulated in a sPLA2 hydrolysable liposome can be used therapeutically, argues that other antineoplastic agents encapsulated in sPLA2 hydrolysable liposomes can also be used therapeutically, i.e. they will not be released from sPLA2 hydrolysable liposomes at unintended sites at a concentration which would be detrimental to the therapeutic use of sPLA2 hydrolysable liposomes encapsulating antineoplastic agents.

In a preferred embodiment, the administration of sPLA2 hydrolysable liposomes comprising a therapeutic agent enables administration of a reduced dose of the therapeutic agent as compared to administration of the free therapeutic agent. This is possible for several reasons. First, liposomal encapsulation of the therapeutic agent prolongs the half-life of the agent. Second, the targeting effect of sPLA2 hydrolysis leads to an increased concentration of the free therapeutic agent at sites of increased sPLA2 levels, e.g. at tumours.

In another preferred embodiment, the administration of sPLA2 hydrolysable liposomes comprising a therapeutic agent enables administration of an increased dose of therapeutic agent as compared to administration of the free therapeutic agent. This is possible because of the targeting effect of sPLA2 hydrolysable liposomes and can e.g. be seen by reduced nephrotoxicity of cisplatin encapsulated in sPLA2 hydrolysable liposomes as compared to free cisplatin.

LiPlaCis have been studied in a number of non-clinical toxicology studies in rats and mice. The overall purpose of these studies was to determine both the single dose and multiple dose Maximum Tolerated Dose (MTD) in the two species. These studies were conducted according to Good Laboratory Practice (GLP). In these studies the two species was found to be equally sensitive to LiPlaCis and by applying FDA rules (Reference: Guidance for Industry. Estimating the Maximum Safe Starting Dose in Initial Clinical Trials for Therapeutics in Adult Healthy Volunteers. FDA, July 2005), the human equivalent maximum tolerated dose is predicted to be 30 mg per treatment cycle. Thus, a human MTD of 80 mg or more per treatment cycle is surprising.

Preferred doses of encapsulated cisplatin are between 80 mg and 120 mg per treatment cycle with a 3 week interval, between 120 and 160 mg per treatment cycle with a 3 week interval, between 160 mg and 200 mg per treatment cycle with a 3 week interval, between 200 mg and 240 mg per treatment cycle with a 3 week interval and between 240 mg and 300 mg per treatment cycle with a 3 week interval.

The time between administrations of therapeutic agent may also be adjusted in line with the discussion of reduced/increased doses of therapeutic agent. Thus, in one embodiment, the time between administrations of therapeutic agent is prolonged as compared to the time between administrations of the free therapeutic agent. In another embodiment, the time between administrations of therapeutic agent is reduced as compared to the time between administrations of the free therapeutic agent. When the therapeutic agent is cisplatin, the time between administrations may e.g. be more than 3 weeks or less than 3 weeks.

Preferably, the disease to be treated according the invention is cancer or inflammation, preferably cancer.

Method of Treatment

A second aspect of the present invention is a method of treatment comprising administering an effective amount of an sPLA2 hydrolysable liposome as described in the first aspect of the invention to a patient in need thereof. Specific embodiments of this aspect will be apparent from the first aspect of the invention.

Method of Reducing Nephrotoxicity

A third aspect of the invention is a method of reducing the nephrotoxicity of a therapeutic agent, said method comprising encapsulating the therapeutic agent in a sPLA2 hydrolysable liposome. Preferably, the therapeutic agent is an antineoplastic agent such as cisplatin and preferably, the therapeutic agent is administered to a patient in need thereof. Other embodiments will be apparent from the first aspect of the invention.

Method of Reducing Neurotoxicity

A forth aspect of the invention is a method of reducing the neurotoxicity of a therapeutic agent, said method comprising encapsulating the therapeutic agent in a sPLA2 hydrolysable liposome. Preferably, the therapeutic agent is an antineoplastic agent such as cisplatin and preferably, the therapeutic agent is administered to a patient in need thereof. Other embodiments will be apparent from the first aspect of the invention.

Method of Reducing Gastrointestinal Toxicity

A fifth aspect of the invention is a method of reducing the gastrointestinal toxicity of a therapeutic agent, said method comprising encapsulating the therapeutic agent in a sPLA2 hydrolysable liposome. Preferably, the therapeutic agent is an antineoplastic agent such as cisplatin and preferably, the therapeutic agent is administered to a patient in need thereof. Other embodiments will be apparent from the first aspect of the invention Method of Prolonging the Therapeutic Effect A sixth aspect of the invention is a method of prolonging the therapeutic effect of a therapeutic agent, said method comprising encapsulating the therapeutic agent in a sPLA2 hydrolysable liposome. Preferably, the therapeutic agent is an antineoplastic agent such as cisplatin and preferably, the therapeutic agent is administered to a patient in need thereof. Other embodiments will be apparent from the first aspect of the invention. References

REFERENCES

Andresen T L, J. S. (2005). Advanced strategies in liposomal cancer therapy: problems and prospects of active and tumor specific drug release. *Prog Lipid Res.*, January; 44(1):68-97. Epub 2005 Jan. 22.
Andresen T L, J. S. (2005). Triggered activation and release of liposomal prodrugs and drugs in cancer tissue by secretory phospholipase A2. *Curr Drug Deliv*, October; 2(4):353-62.

EXAMPLES

Example 1

Preparation of sPLA2 Liposomes (LiPlaCis)

A lipid intermediate is prepared by spray-drying the following a mixture of phospholipids (70/25/5 mol % DSPC/DSPG/DSPE-PEG2000). The lipids are dissolved in methanol and chloroform. The lipid intermediate is hydrated in an aqueous solution of the anti-cancer drug with agitation. At this step the liposomes are formed but they have a broad size distribution and is a mixture of single-layer and multiple-layer liposomes. In order to get a product with a narrow size distribution and mono-layer liposomes the hydration mixture is extruded by passing it through poly-carbonate filters of appropriate pore sizes. To remove un-encapsulated anti-cancer drug the mixture is purified. A number of techniques are available e.g. dialysis, gel-filfration and ultra-filtration. For preparations ranging from a few liters and above ultra-filtration is the preferred method. Preparations intended for parenteral administration must be sterilized e.g. by sterile-filtration.

Example 2

Efficacy in Mice

Methods

NMRI nude female mice (6-8 weeks) were inoculated subcutaneously into the left flank with $1*10^7$ cells of the human breast carcinoma cell line MT-3. Only mice carrying exponentially growing tumors were selected for the study.

Treatment started when tumors had reached a size of 70-80 mm3. Animals received one dose (4 mg/kg cisplatin (Platinol), LiPlaCis or saline) weekly with intra-venous injections into the tail vein starting on day 13 after tumor transplant. Tumor growth was assessed three times a week by measuring two perpendicular diameters and tumor growth was normalized for differing starting sizes by calculating relative tumor volume. Body weight was measured three times a week. Blood samples were taken four days after the first injection to estimate white blood cells and thrombocytes by Coulter counter.

Results:

LiPlaCis was compared with cisplatin and saline in an efficacy study using MT-3 breast xenografts on nude mice. Cisplatin and LiPlaCis were given at a dose of 4 mg/kg weekly. Because of toxicity, only two injections of LiPlaCis were administrated compared to three for cisplatin and saline. LiPlaCis inhibited tumor growth significantly better than free cisplatin (FIG. 1). The effect was apparent a week after of the first dosing and lasted till the experiment was terminated because of large tumors in the control group. One mouse died in the LiPlaCis-treated group.

of the human breast carcinoma cell line MT-3. Only mice carrying exponentially growing tumors were selected for the study. The single dose was given when the tumors had reached a size of at least 300 mm3. Animals received 3 mg/kg cisplatin (Platinol) or LiPlaCis by tail vein injection. The time points were 1, 24, 48, 72 and 168 h. Blood samples (500 µl) was taken immediately before sacrifice and transferred to heparinised tubes (Microvette CB 300 Sarsted), centrifuged and frozen. Post mortem, the tumors, organs and tissues (kidneys, liver, quadriceps muscle on the hind limb and spleen) were dissected, washed in saline and snap frozen. To determine platinum concentrations in plasma and tumors/tissues, the samples were digested in HCl/HNO3/H2O2 (60/5/35 vol %) and subjected to ICP-MS.

Results:

Platinum analysis in plasma showed that LiPlaCis was present at high concentrations in serum and the effect was lasting for at least a week. The levels of LiPlaCis in serum were at any time-point more than an order of magnitude higher than free cisplatin. LiPlaCis also accumulated in tumors with a maximum of about 4 µg/mg tumor mass compared to about 1 µg/mg tumor for free cisplatin. There

TABLE 1

Experimental parameters and toxicity:

| Group | mice | Subst. | Treatment (days) | Dose (mg/kg/inj.) | tox deaths(d) | BWC (%) d 13-24 | Optimum T/C (%) [at day] | WBC d 17 (10^6/ml) | Thromb. d 17 (10^6/ml) |
|---|---|---|---|---|---|---|---|---|---|
| A | 10 | Saline | 13, 20, 27 | | 0 | −2 | | 9.7 +/− 1.2 | 1185 +/− 89 |
| B | 10 | Cisplatin | 13, 20, 27 | 4 | 0 | −6 | 71 [31] | 10.6 +/− 1.5 | 1201 +/− 117 |
| C | 10 | LiPlaCis | 13, 20 | 4 | 1 (26) | −14 | 31 [26]*+ | 11.2 +/− 2.7 | 1058 +/− 183 |

BWC: Body Weight Count, difference in percentage compared to the weight before treatment.
Optimum T/C: Quote of treated tumors divided with control tumors.
WBC: White Blood Cells
Thromb: Thrombocytes
LiPlaCis appears to lead to higher bioavailability of cisplatin and induce more potent anti-tumor efficacy but has more intense side effects than free cisplatin including body weight loss and thrombopenia.

Example 3

Pharmacokinetics in Rats

Methods:

Rats (BrlHan:WIST@Mol(GALAS)) were injected with 3 mg/kg cisplatin or LiPlaCis and blood was collected into heparinised tubes (Microvette CB 300 Sarsted). Samples were taken from 10 minutes up to 72 h. A blood volume of 250 µl was taken from each sampling point and immediately placed in an ice-bath and centrifuged (3000×g; 5 min) to obtain the plasma fraction. The plasma-containing tubes were frozen until shipment and subsequent digestion in HCl/HNO3/H2O2 (60/5/35 vol %) before platinum analysis using ICP-MS.

Figure 2:
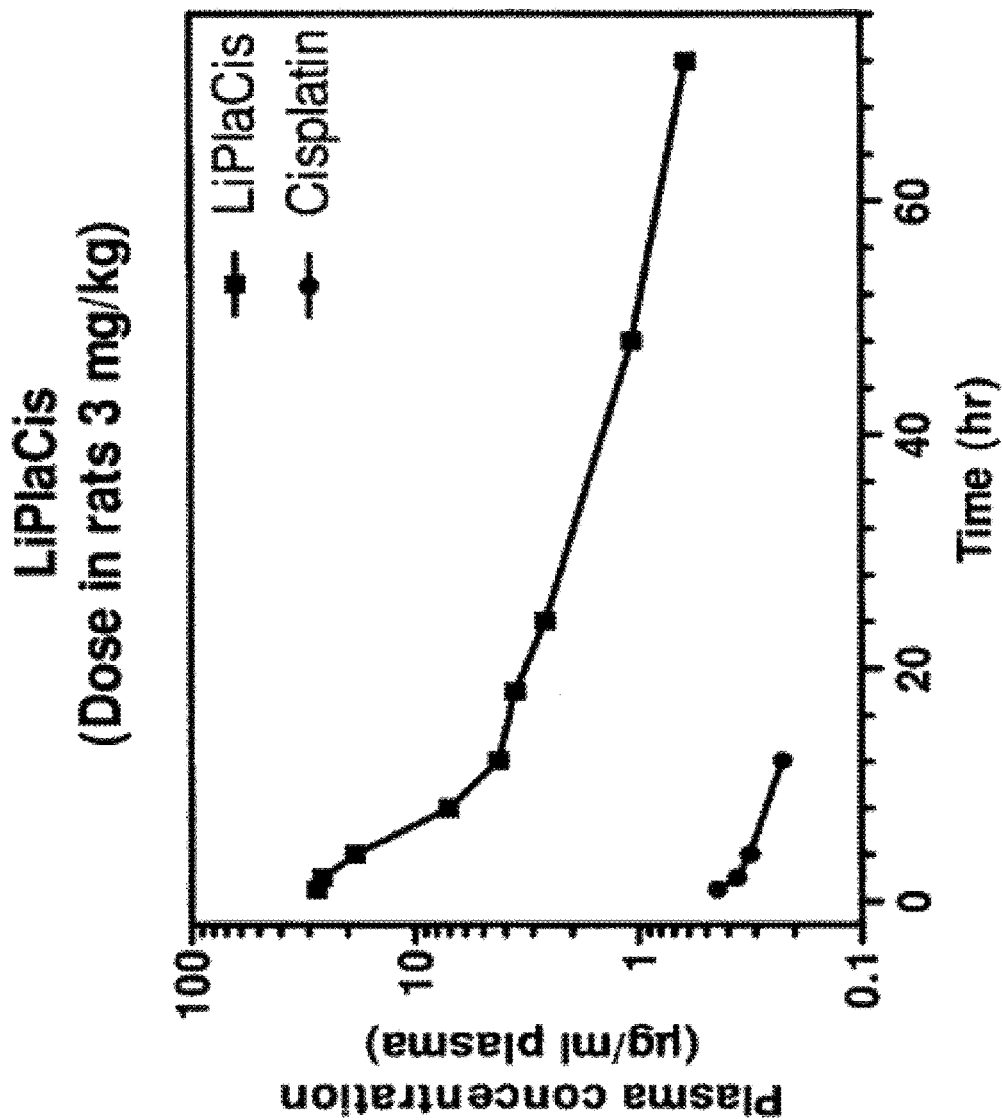
Figure 3:
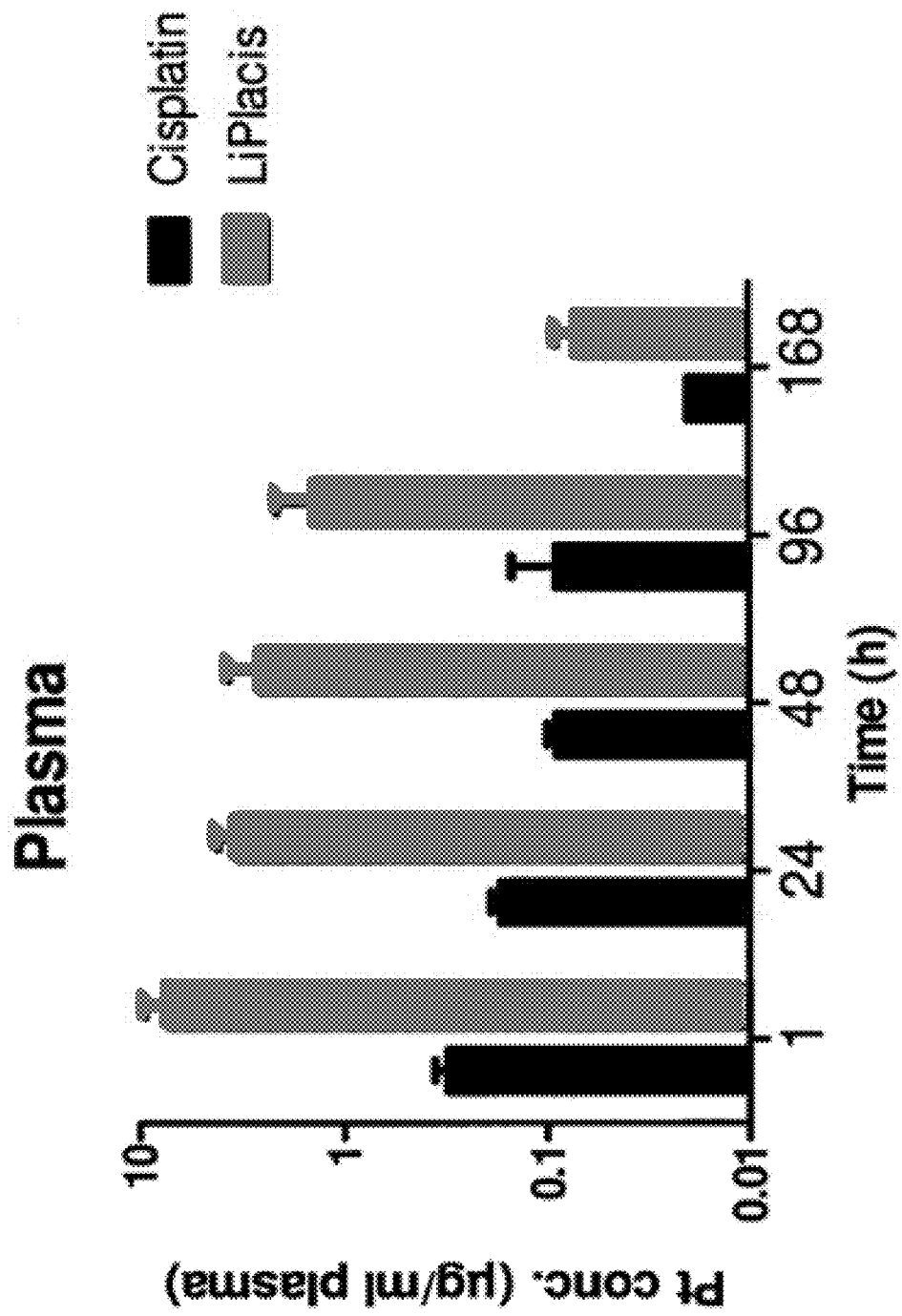
Figure 4:
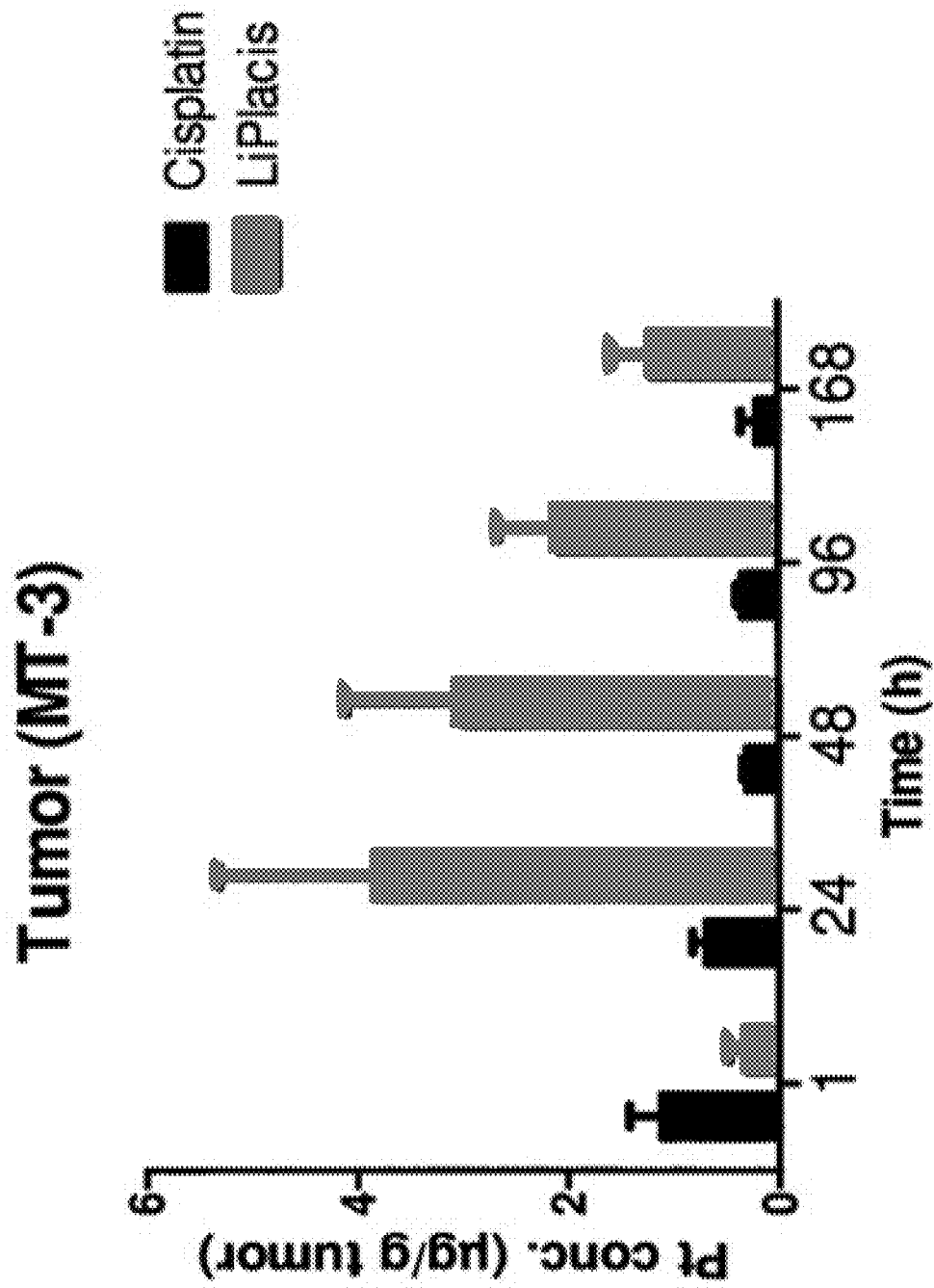
Figure 5:
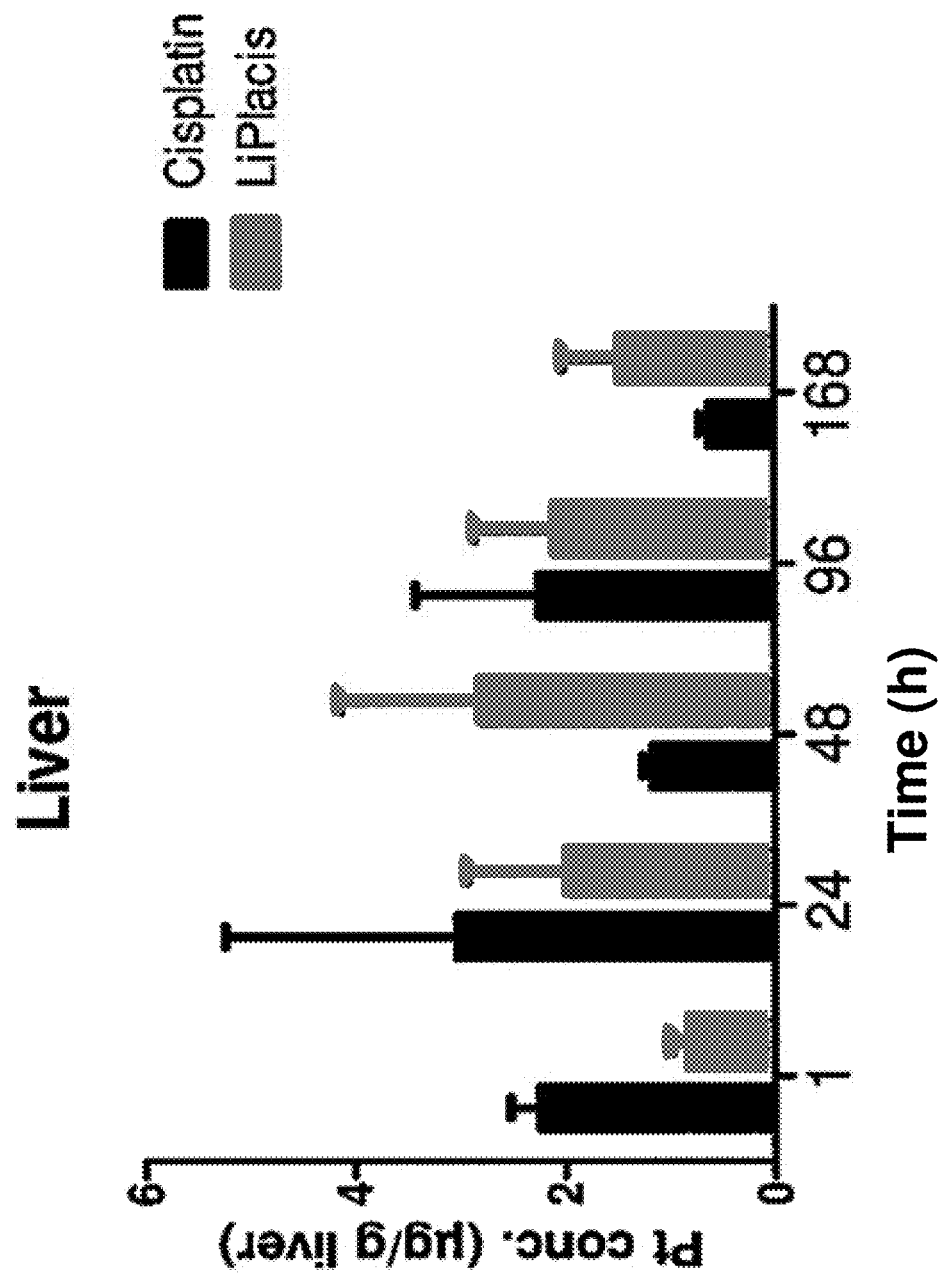
Figure 6:
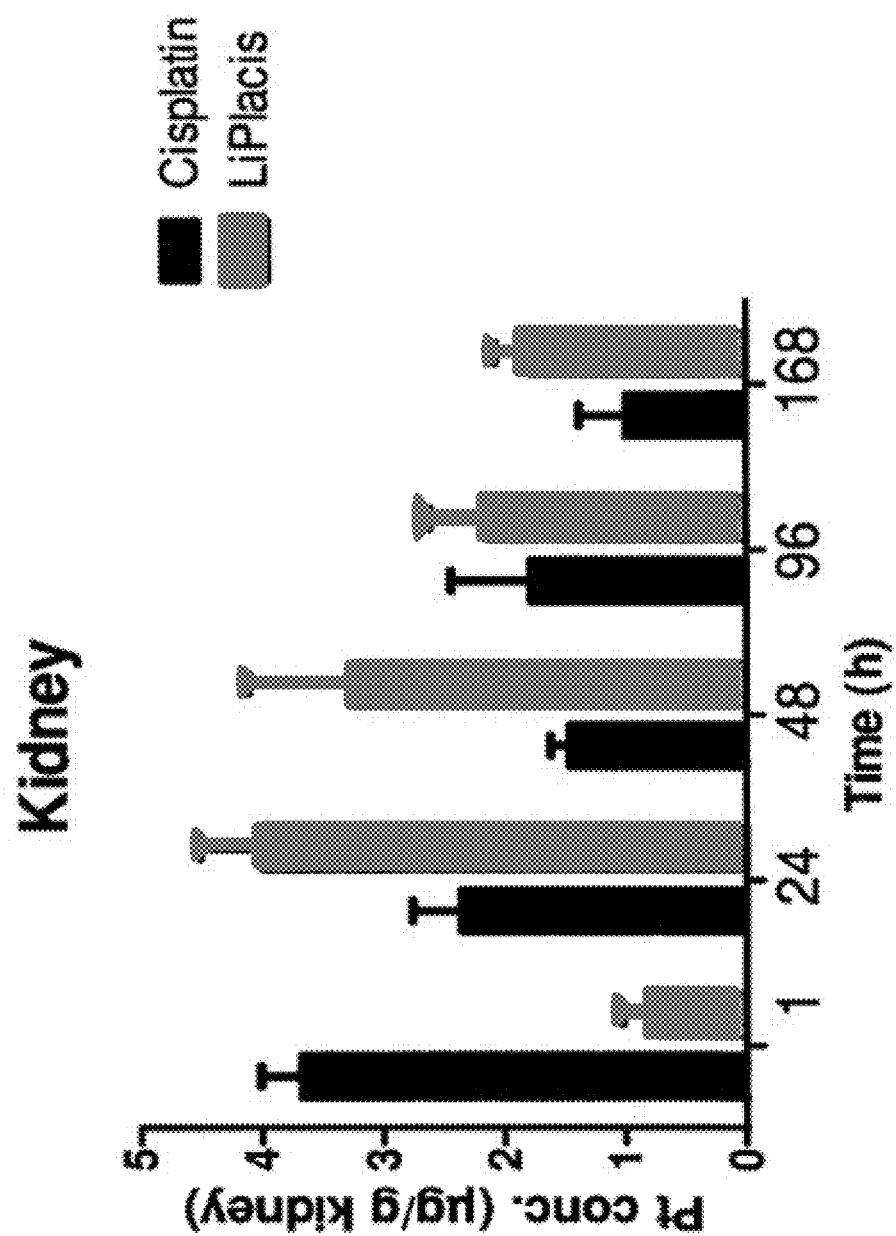
Figure 7:
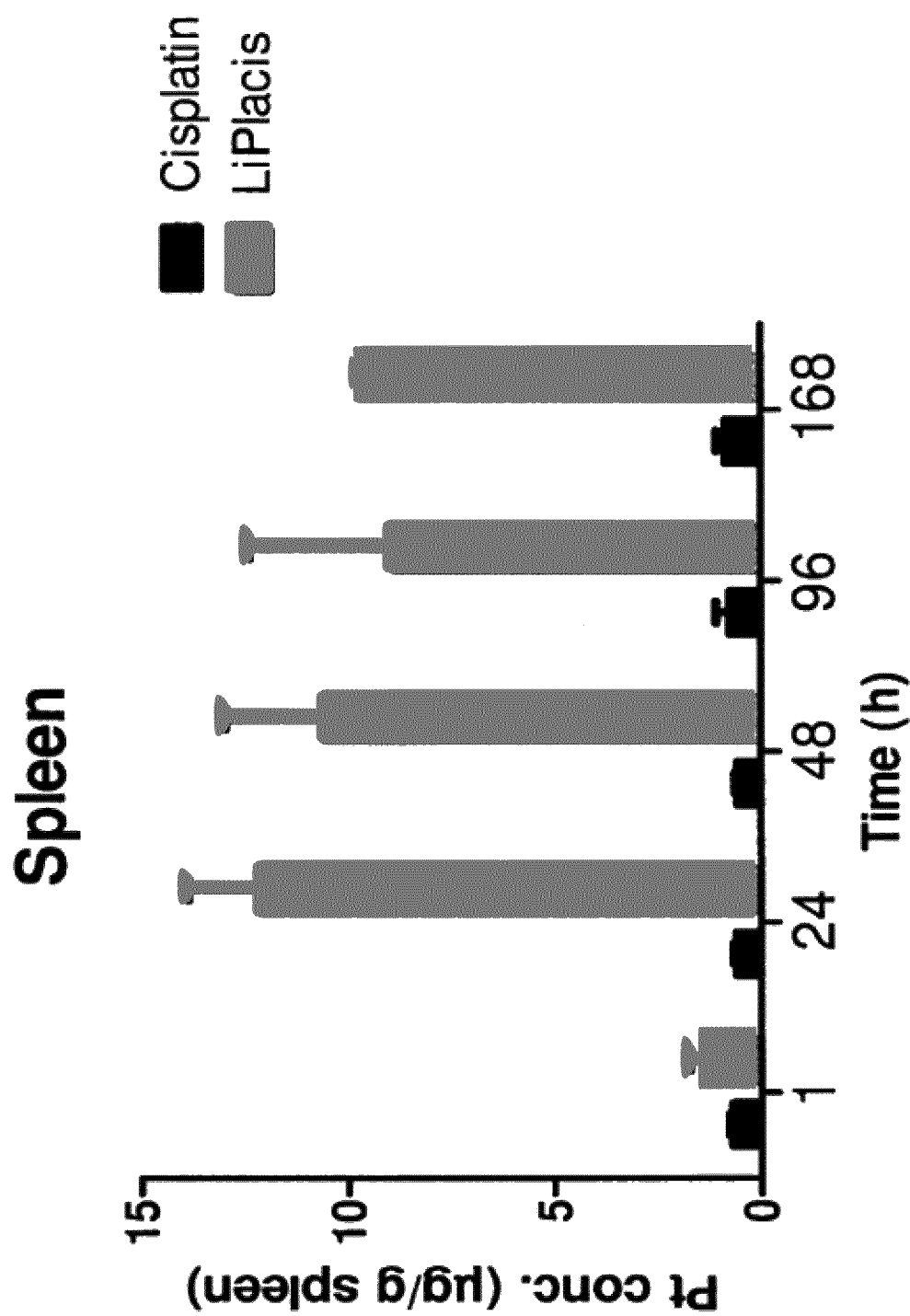
Figure 8:
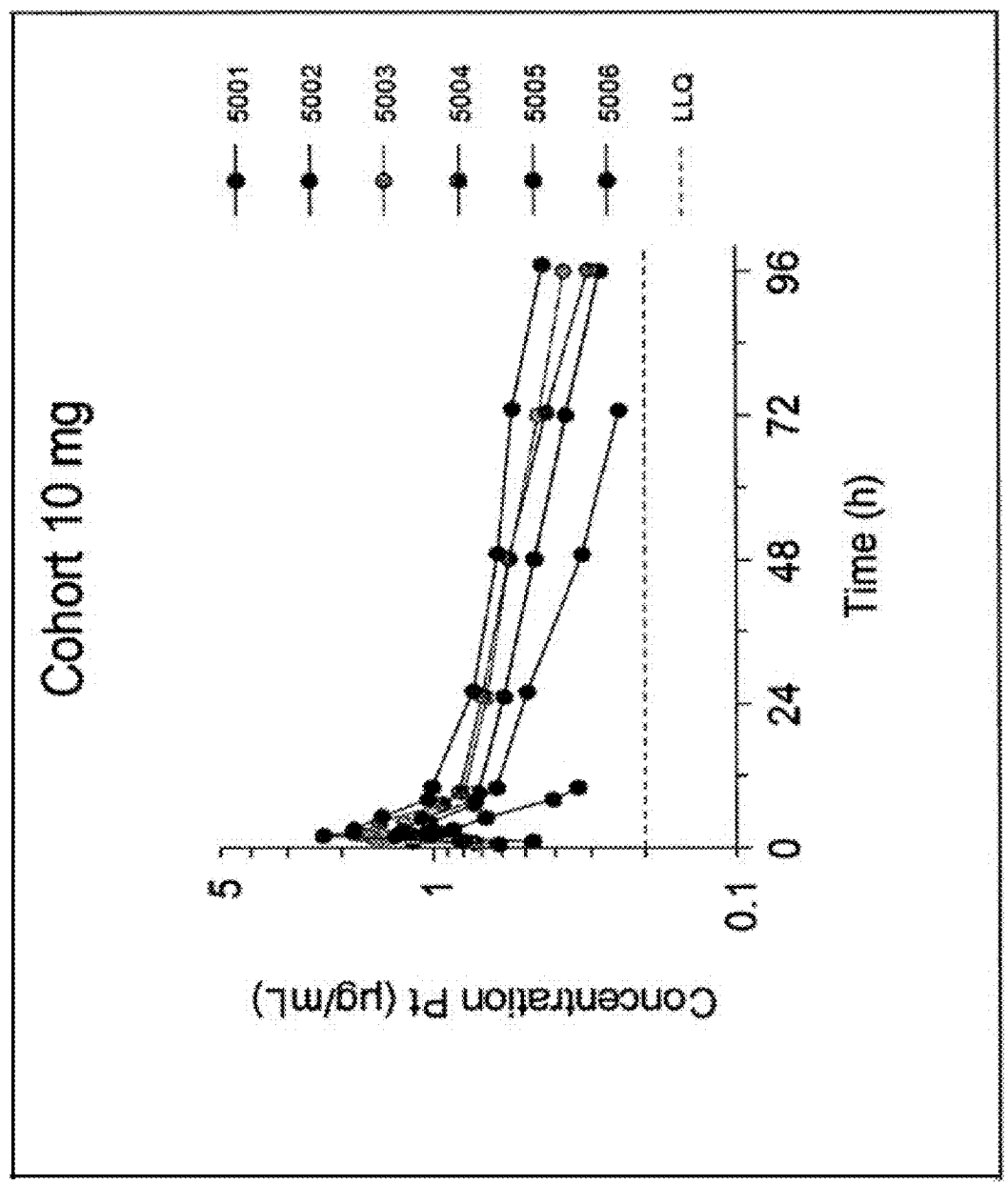
Figure 9:
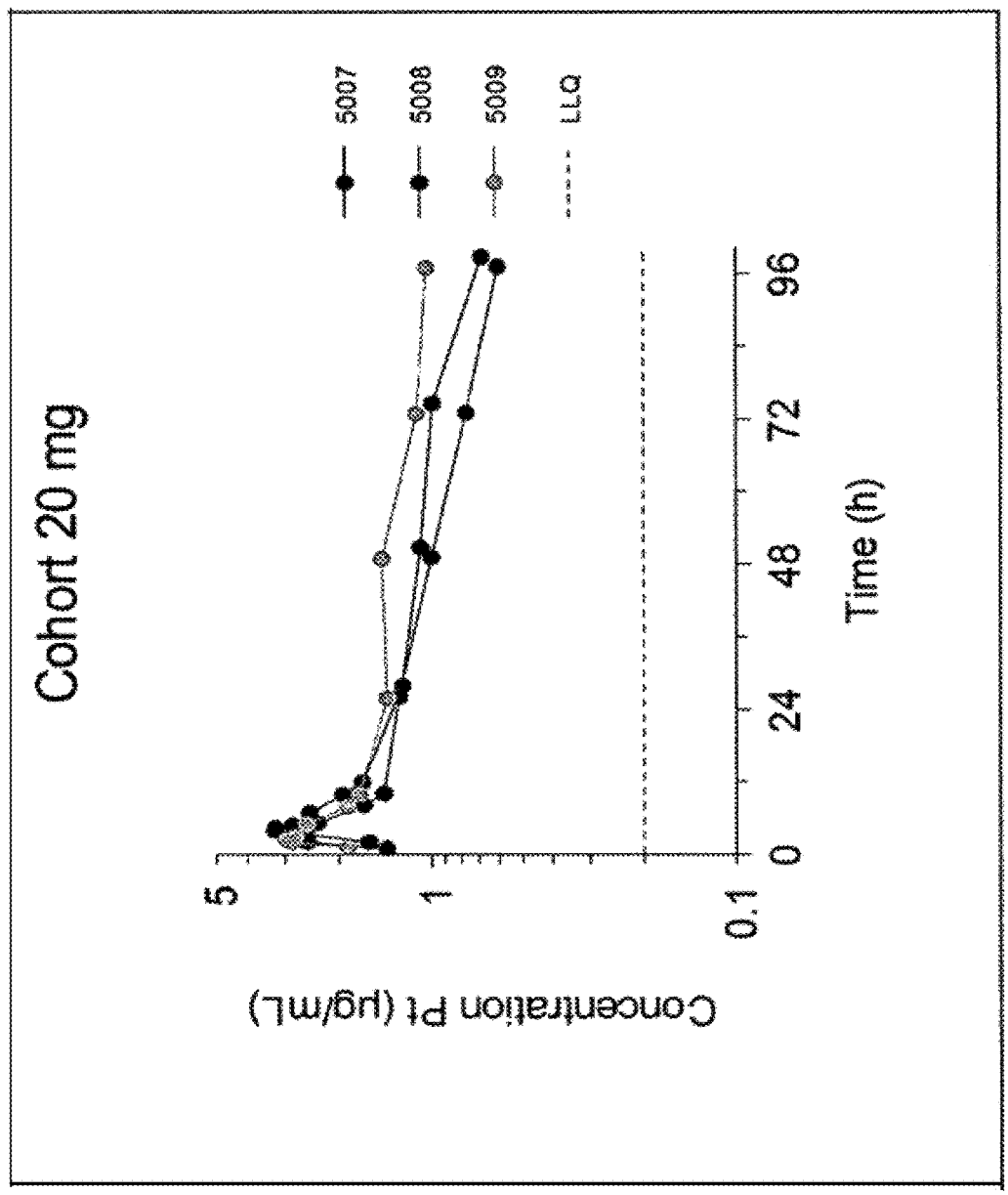
Figure 10:
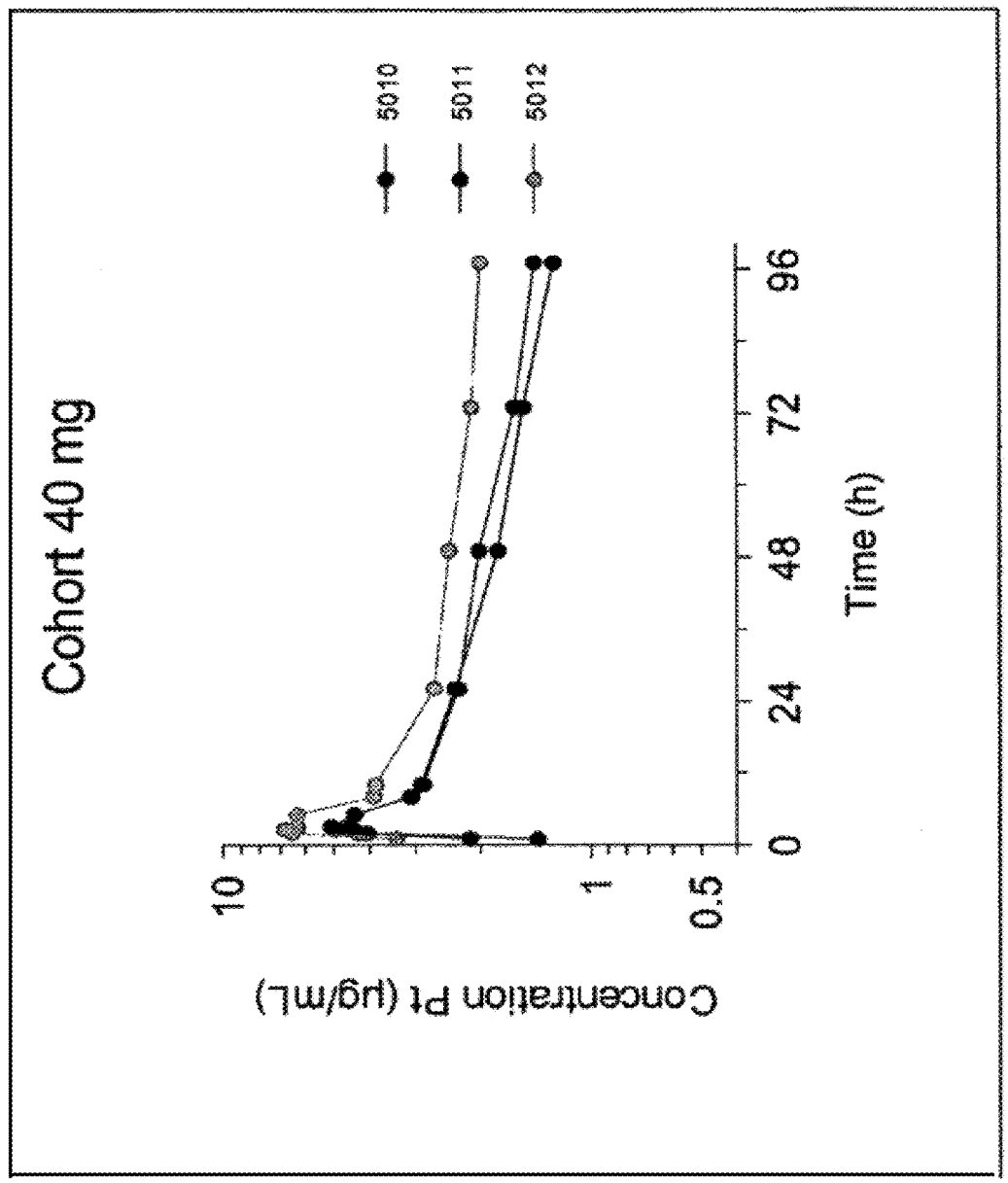
Figure 11:
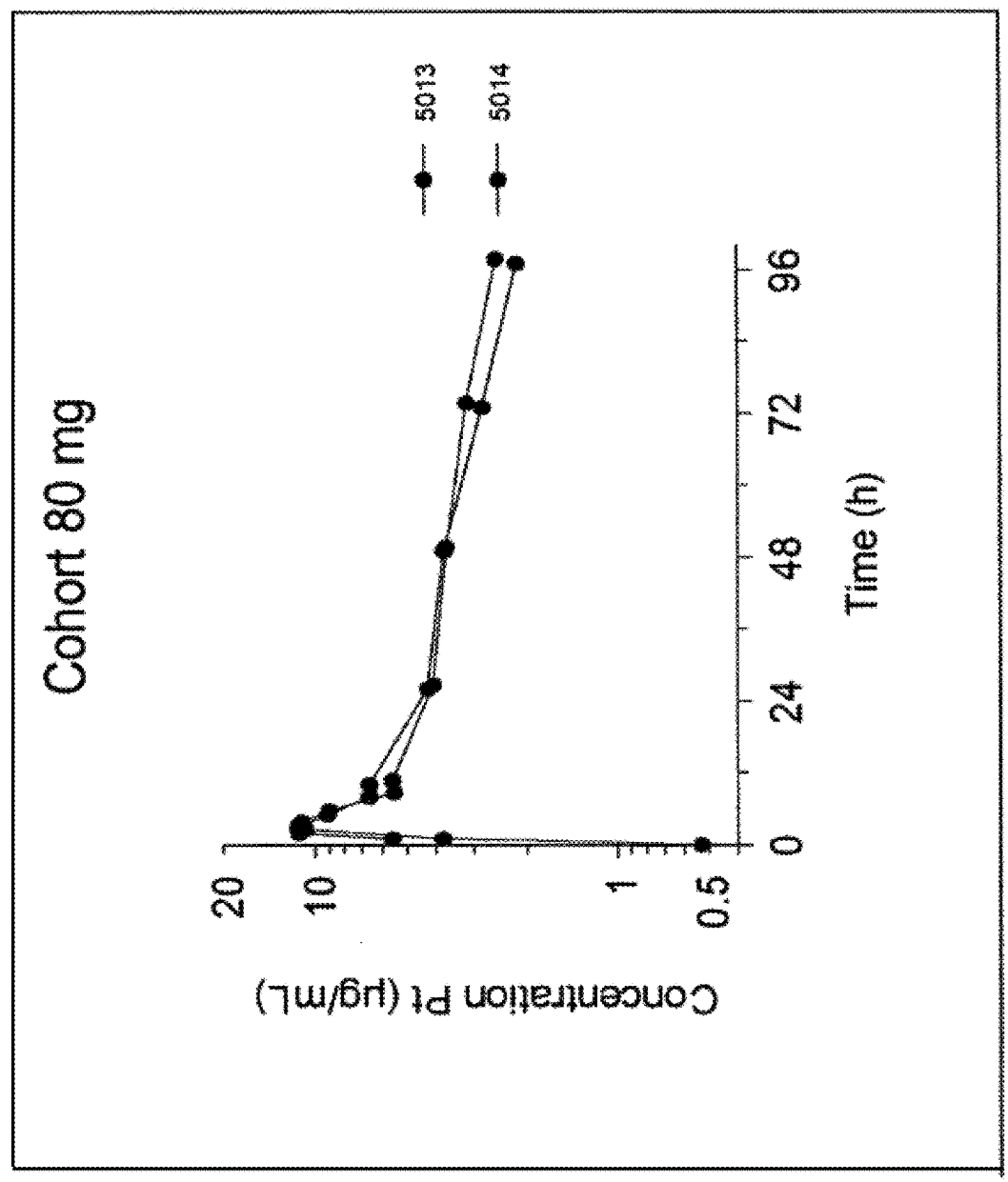

Results and Conclusion:

The experiment revealed that LiPlaCis is a long-circulating liposomal form of cisplatin with a T1/2 of about 20-23 h compared to the 15 minutes for free cisplatin. The area under the curve (AUC) for LiPlaCis was at least 50 times that of cisplatin. See FIG. 2.

Example 4

PK/BD in Nude Mice

Methods:

Nude BALB/c female mice (6-8 weeks) were inoculated subcutaneously into the left and right flank with $1 \times 10^7$ cells were no significant differences in platinum accumulation in the liver. There was a moderate accumulation of LiPlaCis in the kidneys whereas the highest levels of platinum could be measured in the spleen from LiPlaCis-treated animals. See FIGS. 3-7.

Conclusion PK/BD:

LiPlaCis is long-circulating liposomal form of cisplatin. LiPlaCis accumulates in tumors and also in kidneys and spleen. Cisplatin can be released from LiPlaCis in the tumor microenvironment Example 5

Nephrotoxicity

In humans receiving cisplatin therapeutically, a major side effect and the dose limiting toxicity of cisplatin is nephrotoxicity. In this study the nephrotoxicity of cisplatin was compared with that of LiPlaCis in the rat.

Methods

Groups of five male and five female Wistar rats, 6-7 weeks old and with a body weight of 145-175 g, were given an intravenous injection of either 3 mg/kg of Cisplatin or 3 mg/kg of LiPlaCis.

Two days after the injection, two males and two females from each group were sacrificed, 7 days after the injection, one male and one female from each group were sacrificed, and 14 days after the injection the remaining two males and two females from each group were sacrificed. The animals were subjected to macroscopic pathology and absolute and relative kidney weights were recorded. Histopathology was performed on kidneys, urinary bladder and spleen from all animals.

Results and Conclusion

At necropsy, the kidney weights were generally higher after treatment with LiPlaCis, and the histopathological examination showed that treatment with LiPlaCis clearly reduced the severity of renal degenerative changes in the form of multifocal tubular basophilia/debris and diffuse tubular vacuolation and dilation. Treatment with LiPlaCis presumably also caused a lower incidence of decreased cellular density of the white pulp/periarterial sheath compared with Cisplatin. In conclusion, LiPlaCis clearly reduced the nephrotoxicity of Cisplatin in rats.

Example 6

Phase I Dose-Escalating Study to Evaluate the Safety and Tolerability of LiPlaCis (Liposomal Cisplatin Formulation) in Patients with Advanced or Refractory Tumors Study Synopsis
Primary Objective:
1. To evaluate the safety and tolerability of LiPlaCis given every 3 weeks
2. To determine the maximum tolerated dose (MTD) and the recommended dose (RD) of LiPlaCis given every 3 weeks
Secondary Objectives:
3. To evaluate the pharmacokinetics (PK) of LiPlaCis given every 3 weeks
4. To evaluate the therapeutic efficacy of LiPlaCis given every 3 weeks
Study Design:
Open label, non-randomised dose escalation study
Study Population:
Subjects with a solid tumor not amenable to standard treatment
Number of Patients:
The precise number of patients cannot be defined, as this is dependent on the observed toxicity. Cohorts of 3 to 6 patients will be treated at each dose level until MTD is reached. It is anticipated that 30 patients could be needed to assess MTD.
Eligibility
Inclusion Criteria:
1. Histological or cytological documented locally advanced or metastatic solid tumor refractory to standard therapy or for which no curative therapy exists.
2. Be ≥18 years of age.
3. Have a life expectancy ≥3 months.
4. Have an ECOG performance status of 0-2.
5. Have recovered to grade 1 or less from acute toxicities of prior treatment:
6. ≥6 months must have elapsed since patient received cisplatin.
7. ≥4 weeks must have elapsed since patient received any investigational medicinal product.
8. ≥4 weeks must have elapsed since patient received any radiotherapy, or treatment with cytotoxic or biologic agents weeks for mitomycin or nitrosoureas). No hormonal treatment is allowed except treatment with corticosteroids at physiological dose and hormonal treatment with LHRH agonists for prostate cancer.
9. ≥2 weeks must have elapsed since any prior surgery, blood transfusions or therapy with GM-CSF. However, current use of erythropoietin will be permitted.
10. Be in adequate condition as evidenced by the following clinical laboratory values:
    a. Absolute neutrophil count (ANC) ≥1.5×109/L
    b. Haemoglobin is at least 9 g/dl (5.6 mmol/L)
    c. Platelets ≥100×109/L
    d. Alanine aminotransferase (ALT) and aspartate aminotransferase (AST) ≤2.5×ULN; in case of known liver metastases ALT and AST ≤5×ULN
    e. Serum bilirubin ≤1.5 ULN
    f. Alkaline phosphatase ≤2.5×ULN
    g. Creatinine and blood urea within normal limits, unless creatinine clearance is within normal limits (≥60 mL/min calculated according to Cockcroft-Gault formula) (see appendix 1)
11. Patients (male and female) must be willing to practice an effective method of birth control during the study.
12. Patient or legal representative must understand the investigational nature of this study and sign an independent ethical committee (IEC) approved written informed consent form prior to treatment.
Exclusion Criteria are the Following:
1. Active uncontrolled bleeding or bleeding diathesis (e.g., active peptic ulcer disease).
2. Any active infection requiring parenteral or oral antibiotic treatment.
3. Known infection with human immunodeficiency virus (HIV) or hepatitis virus.
4. Active heart disease including myocardial infarction or congestive heart failure within the previous 6 months, symptomatic coronary artery disease, or symptomatic arrhythmias currently requiring medication.
5. Known or suspected active central nervous system (CNS) metastasis. (Patients stable 8 weeks after completion of treatment for CNS metastasis are eligible.)
6. Autoimmune disease.
7. Impending or symptomatic spinal cord compression or carcinomatous meningitis.
8. Having pre-existing neuropathy, i.e., Grade >1 neuromotor or neurosensory toxicity (as defined by National Cancer Institute Common Toxicity Criteria for Adverse Events (NCI CTCAE) v3.0), except for abnormalities due to cancer.
9. Having known hypersensitivity to cisplatin or liposomes.
10. Requiring immediate palliative treatment of any kind including surgery and/or radiotherapy.
11. Female patients who are pregnant or breast-feeding (pregnancy test with a positive result before study entry).
12. Unwilling or unable to follow protocol requirements.
Study Procedures:
Adverse events (AEs): From signing informed consent of study drug until 30 days after receiving the last dose of study drug. Related AEs, incl. serious AEs, are followed until returned to baseline or grade to grade 1.

Physical examination, vital signs, Performance status, Blood chemistry, Urinalysis: baseline and weekly in each cycle.

Haematology: baseline, bi-weekly in cycle 1 and weekly in other cycles.

Pharmacokinetic (PK) sampling: blood and urine samples should be obtained for PK evaluation. Please see section 6.4 Clinical Pharmacology Procedures.

Tumor assessments: baseline and every 3 cycles.

Study Assessments:

Safety, as determined by physical examinations, laboratory toxicity, and the incidence and severity of adverse events.

Safety assessments: NCI Common Technology Criteria for Adverse Events (CTCAE) version 3.0, laboratory evaluations (biochemistry, haematology), vital signs, physical examination including neurological examination, ECOG performance status and body weight.

Maximum tolerated dose of LiPlaCis as determined by dose-limiting toxicities (DLTs) and the recommended dose.

Clinical response rate will be determined by radiographic criteria using RECIST.

Efficacy assessments (if applicable): overall tumor response according to RECIST (CR, PR, SD or PD).

Rationale for the Study

Rationale for Selecting Dose and Schedule:

The human starting dose is determined by using the approach suggested by FDA (Reference: Guidance for Industry. Estimating the Maximum Safe Starting Dose in Initial Clinical Trials for Therapeutics in Adult Healthy Volunteers. FDA, July 2005). Rat MTD is 3 mg/kg and the conversion factor between rat and human is 6.3 according to FDA's guideline. This gives a human equivalent dose (HED) of 0.5 mg/kg.

Mouse MTD is 6 mg/kg and the conversion factor between mouse and human is 12.3 according to FDA's guideline. This gives a human equivalent dose (HED) of 0.5 mg/kg.

Thus, when the rat and mouse MTD's are converted into human equivalent doses is evident that these two species have the same sensitivity when exposed to LiPlaCis.

The reference human body weight is according to the guideline 60 kg which correspond to a dose of 30 mg per patient (0.5 mg/kg*60 kg=30 mg).

A safety factor of 3 is applied resulting in a starting dose of 10 mg per patient. This dose represents 1/10 of the recommended lowest dose of plain cisplatin products (50 to 100 mg/m2 when administered as a single dose every 3-4 weeks) assumed that a normal person's body surface area is 2 m2.

A higher safety factor is frequently used (often 10) but the findings in the non-clinical studies suggest that the toxicity of LiPlaCis is determined by the intrinsic toxicity of cisplatin and that LiPlaCis is less toxic compared to plain cisplatin.

Starting at 10 mg per subject should then be well on the safe side. Further it should be noted that LiPlaCis is not a completely new drug, but a new formulation of a very well known and widely used drug.

Rationale for Schedule and Route of Administration:

In previous clinical phase I and II studies of liposomal cisplatin formulations—e.g. SPI-077 and Lipoplatin developed by ALZA Corp. and Regulon Inc., respectively—the drug product has mainly been administered every three weeks and the median number of cycles given has been between 2 and 4. In some of these studies, patients were to receive a total of 6 cycles.

To ensure that patients can be treated optimally in terms of safety and potential efficacy, LiPlaCis will be administered every 3 weeks for up to 3 cycles or more if the patient benefits from further cycles in the opinion of the investigator.

LiPlaCis will be administered intravenously by infusion as conventional cisplatin.

Study Description

The study is an open label, dose-escalating, non-randomised phase I study of LiPlaCis in patients with advanced cancer.

LiPlaCis will be administered every 3 weeks for up to 3 cycles or more if the patient benefits from the treatment upon the investigator's judgement and if there is no evidence of progressive disease or unacceptable toxicity.

Post-trial access to other care must be evaluated when patients enter the trial.

LiPlaCis will be administered with increases of 20 to 100% from the previous dose level.

The number of levels needed to reach MTD is unknown. The dose escalation of 20 to 100% will be made based on toxicity and pharmacokinetics after discussion between the investigators and the sponsor.

A clinical (telephone) conference will be organized once the last patient in the respective cohort has completed the first cycle to discuss dose-escalation. The same panel of investigators in discussion with the sponsor (LiPlasome Pharma) will decide on the MTD and the recommended dose (RD) to be used in future phase II studies of LiPlaCis.

The MTD will be the regimen with two or more patients with DLT in a cohort of 3 or 6 patients. Following completion of all cohorts and after the MTD has been defined; a clinical conference will be organized to review the outcomes of the patients to decide on the next dose, and to determine the RD for LiPlaCis. The RD will normally be the dose level below MTD (MTD-1). RD will be the dose at which no more than 1 out of the 6 patients experience DLT in first cycle.

Three patients will be enrolled per dose level and each cohort of patients will receive LiPlaCis every 3 weeks to a total of three cycles or more or until disease progression or unacceptable toxicity occurs (please see definition of dose-liming toxicity in section 6.5). Per cohort/dose level the second and third patient can be entered simultaneously after evaluation of the first week of the 1st cycle of the first patient in that cohort.

The duration of infusion will be 1 hour and could be changed to 3 hours in case adverse events—e.g. infusion reactions—necessitate a longer duration or a temporary discontinuation of infusion.

If a dose-limiting toxicity (DLT) occurs in one of the three patients within one cohort, then three additional patients will be treated at that level. If a DLT occurs in 2/3 or 2/6 patients, the next lower dose level will be expanded to at least 6 patients. The last patients of a cohort will be observed for 3 weeks before accrual to the next higher dose level might start.

Patients will be replaced within a cohort when they go off study within 3 weeks for other reason than toxicity.

The last patient at a dose level should be observed for at least 3 weeks before the first patient at the subsequent dose level can be treated.

Antiemetics:

Initially, the study treatment will start without the use of prophylactic anti-emetics. Once two patients experience nausea and/or vomiting grade 2 or more, prophylactic use of the following anti-emetics will be introduced for the patient in question and the remaining patients.

Step 1: 5-HT3 antagonist (e.g. granisetron, ondansetron)

Step 2: Day 1: granisetron 1 mg iv and dexamethason 10 mg iv, Day2-4: dexamethason 6 mg per os Step 3: Day 1: aprepitant 125 mg per os, granisetron 1 mg iv, dexamethason 10 mg iv; Day2-3: prepitant 80 mg per os, dexamethason 6 mg per os; Day 4: dexamethason 6 mg per os.

If a patient experiences nausea and/or vomiting of grade 2 or more, therapeutic anti-emetics may be administered including Step 0: metoclopramide. At re-treatment this patient may receive prophylactic anti-emetics at investigators decision. The anti-emetics will be administered in accordance with procedures at Erasmus MC and LUMC.

Hydration:

Hydration will not be used routinely.

However, if nephrotoxicity is observed in a patient, both pre- and post-hydration will be introduced for the remaining cycles of this patient Hydration will consist of 1000 mL glucose 2.5%/NaCl 0.45% over 4 hours prior to treatment and 3000 mL glucose 2.5%/NaCl 0.45% over 8 hours post treatment.

In accordance with the definition of MTD in case nephrotoxicity should be observed in two or more patients in a cohort of 3 or 6 patients pre- and post-hydration will be introduced for the remaining cycles of the remaining patients.

However in case nephrotoxicity is observed in different patient over different cohorts this might also be a reason to start with the introduction of additional hydration. This will be decided during dose escalation teleconferences with the investigators and the sponsor.

Study Population

The targeted population for this study are patients with histologically or cytologically documented locally advanced or metastatic solid tumor refractory to standard therapy or for which no curative therapy exists.

Number of Patients

The precise number of patients cannot be defined, as this is dependent on the observed toxicity. Cohorts of 3 to 6 patients will be treated in each cohort until the MTD and the recommended dose for phase II studies of LiPlaCis is determined. It is expected that up to 30 evaluable patients could enter the study to meet the key objectives of the study. However, more patients will be enrolled if required to do so.

Prior to inclusion, the patients must give written informed consent for this study and must meet all the selection criteria listed in section 3.3. Patients who sign an informed consent but fail to meet the inclusion and/or exclusion criteria are defined as screen failures. For all patients who have consented, the investigator is to maintain a screening log that documents the screening number, patient initials, and (if applicable) reason(s) for screen failure. A copy of the log should be retained in the investigator's study file.

Results from Phase 1 Study

PK:

Pharmacokinetic data confirm that LiPlaCis is a long circulatory formulation of cisplatin. The following is observed:

The observed T½ is 78 hours, which is to be compared with cisplatins T½ of less than one hour. See FIGS. 8-11.

Figure 12:
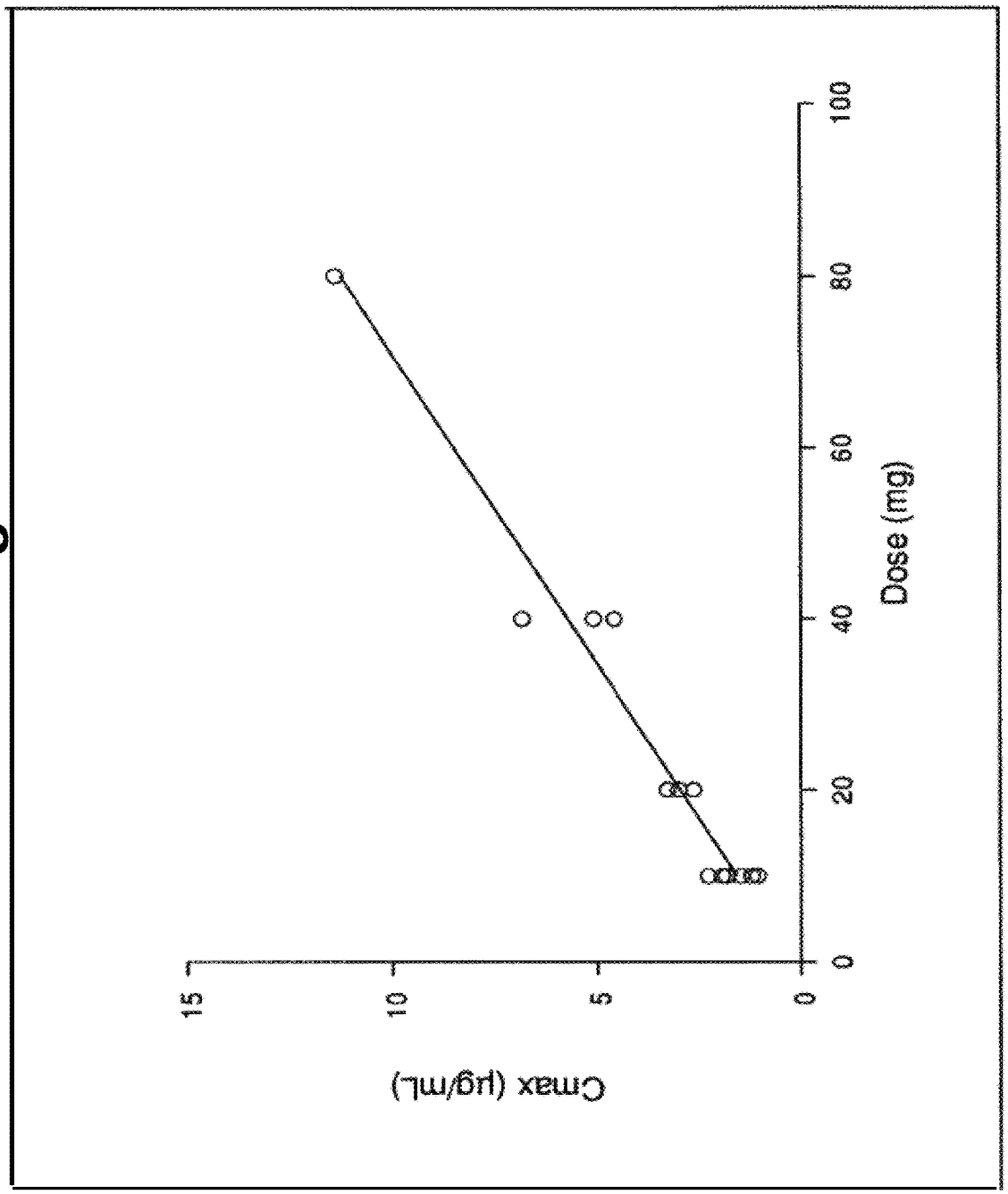
Figure 13:
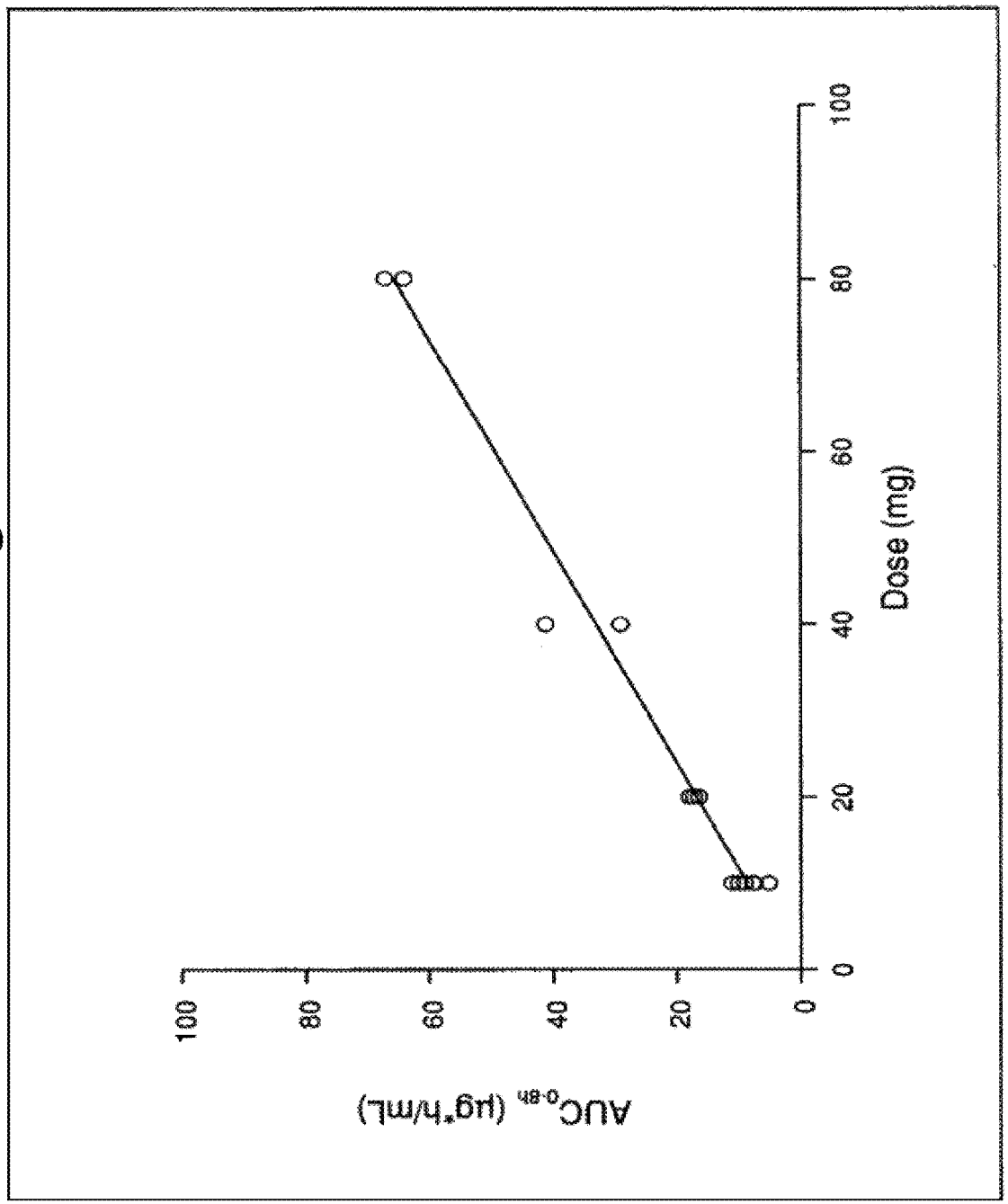
Figure 14:
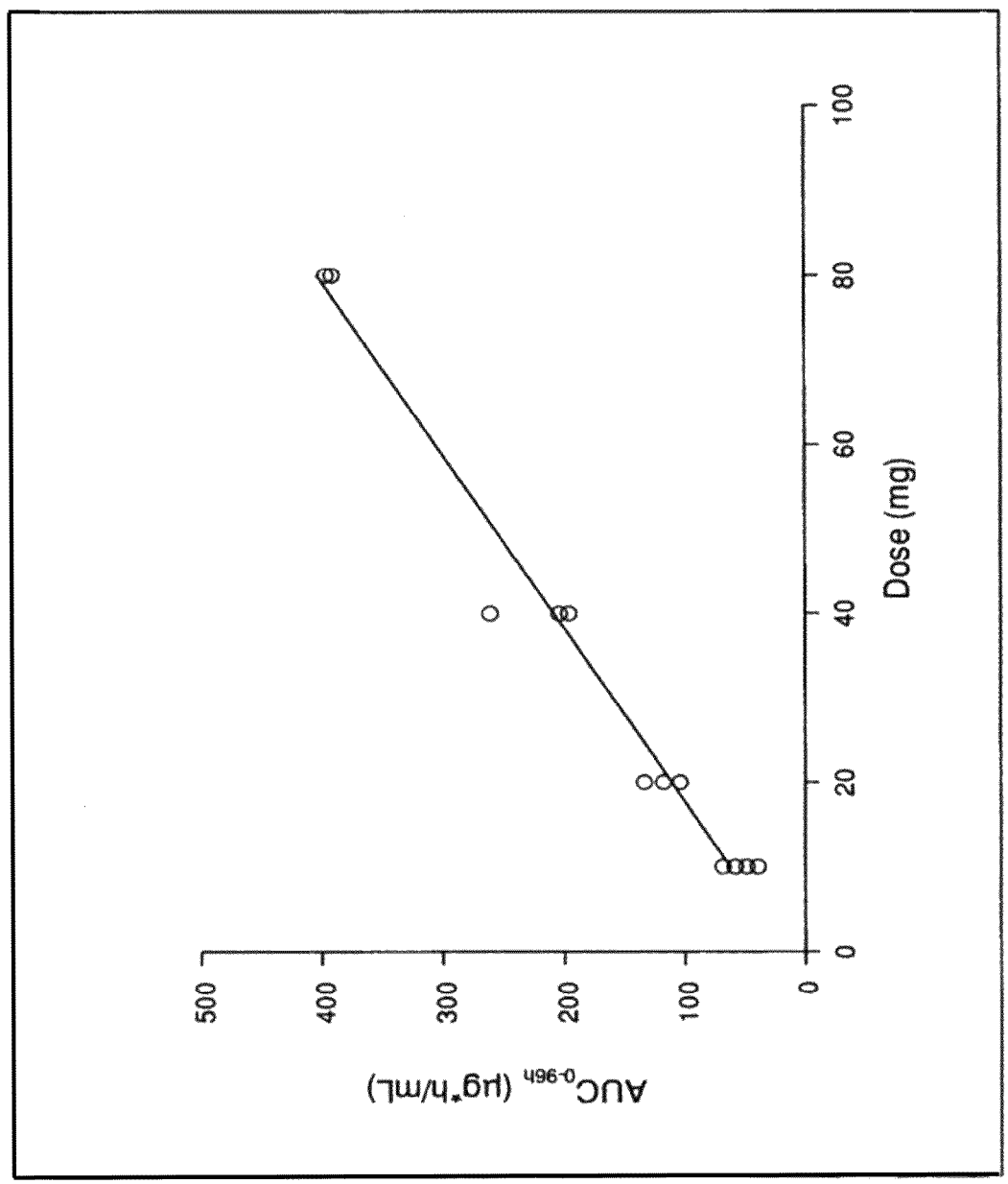

The pharmacokinetic profile is linear both in terms of Cmax and AUC. See FIGS. 12-14.

Urinary excretion is significantly altered compared to cisplatin. Urine is collected from 0 to 96 hours and excretion is between 0 and 20% of the administered dose. Cisplatin urinary excretion is above 90% within 3 hours.

Tox:

LiPlaCis administered in doses up to 120 mg per treatment cycle shows no sign of nephrotoxicity, ototoxicity and neurotixicity. Further, gastrointestinal toxicity in form of nausea and vomiting have not been reported in patients receiving LiPlaCis. See FIGS. 15 and 16A-16E.

The invention claimed is:

1. A method of treating a cancer in a subject in need thereof comprising administering to the subject a composition comprising a secretory phospholipase A2 (sPLA2)-hydrolyzable cisplatin-containing liposome comprising:
    (a) 25% (mol/mol) 1,2-distearoyl-sn-glycero-3-[phospho-rac-(1-glycerol)] (DSPG),
    (b) 5% (mol/mol) 1,2-distearovl-sn-glycero-3-phospho-ethanolamine-N-[methoxy(polyethylene glycol)-2000)] (DSPE-PEG),
    (c) 70% (mol/mol) 1,2-distearoyl-sn-glycero-3-phospho-choline (DSPC),
    (d) less than 1% cholesterol, and
    (e) cisplatin;
    wherein the subject receives an amount of the composition that delivers 80 mg to 120 mg cisplatin per treatment cycle.

2. The method of claim 1, wherein the method comprises at least two treatment cycles.

3. The method of claim 1, wherein each treatment cycle comprises administration of one or two doses of the composition.

4. The method of claim 1, wherein the composition is administered intravenously as a bolus injection or infusion.

5. The method of claim 1, wherein:
    a) an interior of the liposome comprises 0.9% NaCl;
    b) a buffer solution on an exterior of the liposome comprises 10 mM phosphate buffer at pH 6.5, 1 mM NaCl and 10% sucrose; and/or
    c) the liposome is unilamellar.

6. The method of claim 1, wherein the subject exhibits reduced nephrotoxicity and/or reduced nausea and vomiting upon administration of the composition relative to administration of free cisplatin.

7. The method of claim 1, wherein the liposome has a diameter of 50 to 400 nm, 80 to 160 nm, or 90 to 120 nm.

8. The method of claim 1, wherein the composition has a poly dispersity index (PDI) of 0.2 or less.

9. The method of claim 8, wherein the PDI of the composition is 0.10 or less.

10. The method of claim 1, wherein the method comprises two to six treatment cycles.

11. The method of claim 10, wherein the method comprises three treatment cycles.

12. The method of claim 1, wherein the cancer is an advanced or refractory tumor.

13. The method of claim 12, wherein:
    a) the liposome accumulates in the tumor and in kidneys and spleen in an amount that is greater than free cisplatin; or
    b) the liposome releases cisplatin in the tumor microenvironment.

14. The method of claim 1, wherein the composition is administered without hydration.

15. The method of claim 1, wherein the liposome has a half-life that is greater than 24 hours.

16. The method of claim 1, wherein the sPLA2 hydrolyzable cisplatin-containing liposome has a blood half-life of 78 hours.

17. The method of claim 1, wherein administration of the composition to the subject results in a peak plasma concentration (Cmax) of at least 10 µg/mL.

18. The method of claim 1, wherein administration of the composition to the subject results in a plasma concentration having an area under the curve (AUC) of at least 60

μg×h/mL at 8 hours after administration and/or an AUC of at least 400 μg×h/mL at 96 hours after administration.

* * * * *